(12) United States Patent
Bannasch et al.

(10) Patent No.: US 7,608,400 B2
(45) Date of Patent: Oct. 27, 2009

(54) METHODS FOR DETECTING A CYCLOPHILIN B SNP ASSOCIATED WITH HERDA

(75) Inventors: Danika Bannasch, Davis, CA (US); Robert Tryon, Woodland, CA (US); Stephen White, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 143 days.

(21) Appl. No.: 11/787,611

(22) Filed: Apr. 16, 2007

(65) Prior Publication Data

US 2009/0004650 A1 Jan. 1, 2009

Related U.S. Application Data

(60) Provisional application No. 60/826,038, filed on Sep. 18, 2006.

(51) Int. Cl.
*C12Q 1/68* (2006.01)
*C12P 19/34* (2006.01)

(52) U.S. Cl. .......................... 435/6; 435/91.1; 435/91.2

(58) Field of Classification Search ........................ None
See application file for complete search history.

(56) References Cited

U.S. PATENT DOCUMENTS

2007/0105234 A1* 5/2007 Swiderski et al. ........... 436/106

FOREIGN PATENT DOCUMENTS

WO    WO 2008/121727 A1    10/2008

OTHER PUBLICATIONS

Borges et al., "Hereditary Equine Regional Dermal Asthena in Three Related Quarter Horse in Brazil," Veterinary Dermatology, 2005, 16, 125-130.
Davis et al., "Thermal Stability and Folding of Type IV Procollagen and Effect of peptidyl-Protyl *cis-trans*-lsomerase on Folding of the Triple Helix,"The Journal of Biological Chemistry, vol. 264, No. 15, May 25, 2989, 8956-8962.
Hardy et al., "An Inherited Connective Tissue Disease in the Horse," Laboratory Investigation, vol. 59, No. 2, 1988, 253-262.
Tryon et al., "Inheritance of Hereditary Equine Regional Dermal Asthenia in Quarter Horses," AJVR, vol. 66, No. 3, Mar. 2005, 437-442.
White et al., "Hereditary Equine Regional Dermal Asthenia ('hyperelastosis cutis') in 50 Horses: Clinical, Histological, Immunohistological and Ultrastructural Findings," Veterinary Dermatology, 2004, 15, 207-217.
White et al., "Clinical and Pathological Findings in HERDA-affected Foal for 1.5 years of Life," ESVD and ACVD 18, 2007, 36-40.
White et al., "Hsp47 and Cyclophilin B traverse the Endoplasmic Reticulum with Procollagen and Pre-Golgi Intermediate Vesicles," The Journal of Biological Chemistry, vol. 270, No. 31, Aug. 4, 1995, 18323-18328.
Steinmann, et al., "Cyclosporin A Slows Collagen Triple-Helix Formation in Vivo: Indirect Evidence for a Physiologic Role of Peptidy-Prolyl *cis-trans*-lsomerase," The Journal of Biological Chemistry, vol. 266, No. 2, Jan. 15, 1991, 1299-1303.

* cited by examiner

*Primary Examiner*—Young J Kim
(74) *Attorney, Agent, or Firm*—Townsend and Townsend and Crew LLP

(57) ABSTRACT

This invention provides compositions and methods for identification of carriers of Hereditary Equine Regional Dermal Asthenia (HERDA) in equine species. In particular, this invention identifies a single nucleotide polymorphism (SNP) in cyclophlin B that can be used to identify carriers of HERDA and individuals affected by HERDA.

7 Claims, 15 Drawing Sheets

|  | TLN2 | | USP3 | | AHT58 | | SPG21 | | CILP | | |
|---|---|---|---|---|---|---|---|---|---|---|---|
| Human Map (HSA15) | 60.725 MB | | 61.6 MB | | 62.6 MB | | 63.070 MB | | 63.280 MB | | |
| H71 | T | T | G | G | 185 | 185 | 224 | 226 | G | A | INFORMATIVE RECOMBINANTS |
| H48 | C | T | G | G | 185 | 185 | 224 | 226 | G | A | |
| H37 | T | T | G | G | 185 | 185 | 224 | 226 | G | A | |
| H46 | T | T | G | G | 185 | 185 | 224 | 226 | G | A | |
| H30 | T | T | G | G | 185 | 185 | 226 | 228 | G | A | |
| H28 | T | T | G | G | 185 | 185 | 224 | 226 | G | A | |
| H32 | T | T | G | G | 185 | 185 | 226 | 226 | A | A | |
| H50 | T | T | G | G | 185 | 185 | 226 | 226 | A | A | |
| H27 | T | T | G | G | 185 | 185 | 226 | 226 | A | A | |
| H23 | T | T | G | G | 185 | 185 | 226 | 226 | A | A | |
| H33 | T | T | G | G | 185 | 185 | 226 | 226 | A | A | |
| H31 | T | T | G | G | 185 | 185 | 226 | 226 | A | A | |
| H42 | C | T | G | G | 185 | 185 | 226 | 226 | A | A | |
| H45 | C | T | G | G | 185 | 185 | 226 | 226 | A | A | |
| H36 | T | T | G | G | 185 | 185 | 226 | 226 | A | A | HERD |
| H68 | T | T | G | G | 185 | 185 | 226 | 226 | A | A | |
| H69 | T | T | G | G | 185 | 185 | 226 | 226 | A | A | |
| DR79 | C | C | A | A | | | 224 | 226 | G | G | CONTROL |
| DR80 | C | C | A | A | | | 224 | 224 | G | G | |
| DR170 | C | C | A | A | | | 224 | 226 | G | G | |
| DR171 | C | C | A | A | | | 224 | 224 | G | G | |
| DR172 | C | C | A | A | | | 224 | 224 | G | G | |

Fig. 3

```
                    1       *                              35
HERDA               MLRFSGRNMKVLFAAALIVGSVFFLLLPGPSTADE
Equus caballus      MLRFSERNMKVLFAAALIVGSVFFLLLPGPSTADE
Canis familiaris    MLRLSERNMKVLFAAALVVGSVFFLLLPGPSTADE
Bos taurus          MLRLSERNMKILFVAALVVGSVFFLLLPGPSAADE
Homo sapiens        MLRLSERNMKVLLAAALIAGSVFFLLLPGPSAADE
Mus musculus        MLRLSERNMKVLFAAALIVGSVVFLLLPGPSVAND
Rattus norvegicus   MLRLSERNMKVLFAAALIVGSVVFLLLPGPSVAND
Danio rerio         MVRICERRMKFLVAVTLIVGSVVFLLFPSETEADE
Xenopus tropicalis        MKLLVAAALIAGSVIFLLFPGSSVADE
Gallus gallus             MKALVAAT-ALGPALLLLLPAASRADE 36 *                                 70
HERDA               KKKRPKVTVKVYFDLRIGDEDIGRVVIGLFGKTVP
Equus caballus      KKKGPKVTVKVYFDLRIGDEDIGRVVIGLFGKTVP
Canis familiaris    KKKGPKVTVKVYFDLRIGDEDIGRVVIGLFGKTVP
Bos taurus          KKKGPKVTVKVYFDLRIGDEDIGRVVIGLFGKTVP
Homo sapiens        KKKGPKVTVKVYFDLRIGDEDVGRVIFGLFGKTVP
Mus musculus        KKKGPKVTVKVYFDLQIGDESVGRVVFGLFGKTVP
Rattus norvegicus   KKKGPKVTVKVYFDFQIGDEPVGRVTFGLFGKTVP
Danio rerio         KKKGPKVTAKVYFDIKIGDEDAGRIVIGLFGKTVP
Xenopus tropicalis  KKKGPKVTHKVYFDIKIGDEDVGRVVIGLFGKTVP
Gallus gallus       RKKGPKVTAKVFFDLRVGEEDAGRVVIGLFGKTVP 71                              100
HERDA               KTVDNFVALATGEKGFGYKDSKFHRVIKDF
Equus caballus      KTVDNFVALATGEKGFGYKDSKFHRVIKDF
Canis familiaris    KTVDNFVALATGEKGFGYKDSKFHRVIKDF
Bos taurus          KTVDNFVALATGEKGFGYKDSKFHRVIKDF
Homo sapiens        KTVDNFVALATGEKGFGYKNSKFHRVIKDF
Mus musculus        KTVDNFVALATGEKGFGYKNSKFHRVIKDF
Rattus norvegicus   KTVDNFVALATGEKGFGYKNSKFHRVIKDF
Danio rerio         KTTENFLQLATGEKGFGYKGSKFHRVIKDF
Xenopus tropicalis  KTVENFVTLATGEKGFGYKGSKFHRVIKDF
Gallus gallus       KTVENFVALATGEKGFGFKGSKFHRVIKDF
```

Fig. 6

Table 1

| Gene | Primers | Tm | Size | Seq Primer | Base pairs from end | SNP w/ Flanking Sequence |
|---|---|---|---|---|---|---|
| ITGA11 | F: ACCTGTCTTCCTGGCGCCC | 61 | 1.7Kb | R | 77 | Control: CGGTCCCCGCCCTCA |
| | R: CAGCACATGGAAGTTGATCCGA | | | | | HRDA: CGGTCCCAGCCCTCA |
| CILP | F:TGGTGCCTCAACAGGGAGCAG | 60 | 1.5Kb | R | 155 | Control: AGACAGGGTTTATGT |
| | R:CACTTGCTCCAGGGAGACCA | | | | | HRDA: AGACAGGATTTATGT |
| SPG21 | F:VIC-TCATACTCTGACCCCGCTGATC | 58 | 224-228 | N/A | | Control Allele:224 |
| | R: TTTAATTTTCCTTCCCACTCACG | | | | | HRDA Allele: 226 |
| USP3 | F:AGCTTTCACAGCTGACAGGCATA | 60 | 1.7Kb | F | 337 | Control:AACACCCACTCATGT |
| | R:TGAGTGACTGAAGGATGGCATTC | | | | | HRDA: AACACCCGCTCATGT |
| TLN2 | F:CTCGTCAGAAAATCAGTACTTCTC | 59 | 945bp | R | 153 | Control:GGAGAACCCACAAGC |
| | R:CCAATCCCCACCCCAAGATA | | | | | HRDA: GGAGAACTCACAAGC |

Fig. 7

Table 2

| Locus | Chr. | d.f. | $x^2$ test of independence ||
|---|---|---|---|---|
| | | | $x^2$ | P-Value |
| ASB41 | 1 | 6 | 6.3992 | 0.380 |
| HMS15 | 1 | 7 | 27.4681 | 0.0003 |
| HMS7 | 1 | 7 | 21.4342 | 0.003 |
| LEX34 | 5 | 5 | 3.2420 | 0.663 |
| AHT5 | 8 | 6 | 5.3013 | 0.506 |
| COR69 | 13 | 5 | 8.7535 | 0.119 |
| COR002 | 14 | 4 | 3.3490 | 0.501 |
| B-8 | 15 | 8 | 7.9469 | 0.439 |
| AHT2 | 15 | 4 | 6.2828 | 0.179 |
| LEX56 | 16 | 7 | 7.0211 | 0.427 |
| COR32 | 17 | 3 | 3.4948 | 0.321 |
| LEX36 | 19 | 9 | 4.4039 | 0.883 |
| A-17 | 26 | 8 | 4.7455 | 0.785 |

Fig. 8

Table 3

| Sample | Homozygous Wild Type | Heterozygous | Homozygous "Mutant" | Total |
|---|---|---|---|---|
| HERDA | 4 | 0 | 64 | 68 |
| Relatives | 18 | 58 | 0 | 76 |
| Control-QH | 175 | 7 | 0 | 182 |
| Control-QH | 866 | 31 | 0 | 897 |
| Arabian | 18 | 0 | 0 | 18 |
| Draft | 9 | 0 | 0 | 9 |
| Unidentified | 28 | 0 | 0 | 28 |
| Total | 1118 | 96 | 64 | 1278 |

Fig. 9

Table 4

| MPX Name | $T_m$ (°C) | Marker | Conc (µM) | MPX Name | $T_m$ (°C) | Marker | Conc (µM) |
|---|---|---|---|---|---|---|---|
| MPX-4 | 58 | ASB22 | 0.1 | STR1 | 55 | AHT4 | 0.2 |
| | | ASB5 | 0.04 | | 55 | HTG10 | 0.18 |
| | | B-8 | 0.04 | | 55 | HTG4 | 0.1 |
| | | COR003 | 0.03 | | 55 | LEX3 | 0.2 |
| | | COR058 | 0.05 | | 55 | LEX33 | 1.25 |
| | | COR070 | 0.15 | | 60 | AHT5 | 0.13 |
| | | NVHEQ18 | 0.04 | | 60 | ASB17 | 0.25 |
| MPX-5A | 58 | COR069 | 0.12 | | 60 | ASB2 | 0.3 |
| | | COR075 | 0.04 | | 60 | ASB23 | 0.1 |
| | | I-18 | 0.05 | | 60 | HMS6 | 0.3 |
| | | VHL047 | 0.06 | | 60 | HMS7 | 0.3 |
| MPX-6 | 58 | ASB37 | 0.04 | | 60 | VHL20 | 0.25 |
| | | COR002 | 0.1 | STR2 | 55 | AHT2 | 0.08 |
| | | COR032 | 0.04 | | | CA425 | 0.4 |
| | | COR096 | 0.12 | | | CA487 | 0.07 |
| | | LEX54 | 0.12 | | 60 | CA437 | 0.3 |
| | | NVHEQ79 | 0.05 | | | EB2E8 | 0.6 |
| | | UM010 | 0.05 | | | HMS15 | 0.18 |
| | | ASB39 | 0.12 | | | HMS5 | 0.1 |
| MPX-10 | 58 | COR017 | 0.09 | | | HMS6 | 0.24 |
| | | COR031 | 0.05 | | | HTG3 | 0.15 |
| | | COR040 | 0.12 | | | HTG6 | 0.1 |
| | | LEX25 | 0.02 | | | HTG7 | 0.06 |
| | | NVHEQ70 | 0.03 | STR3 | 55 | CA412 | 0.2 |
| MPX-A | 58 | UM037 | 0.1 | | | CA502 | 0.14 |
| | | HTG21 | 0.1 | | | HMS1 | 0.15 |
| | | LEX74 | 0.1 | | 60 | ASB9 | 0.4 |
| | | LEX37 | 0.1 | | | HMS2 | 1 |
| | | COR082 | 0.15 | MPXvgl4-1 | 58 | ASB14 | 0.04 |
| | | COR008 | 0.1 | | | NVHEQ82 | 0.04 |
| MPX-B | 58 | LEX22 | 0.1 | | | A-14 | 0.06 |
| | | L15.2 | 0.1 | | | LEX034 | 0.08 |
| | | COR071 | 0.1 | | | COR007 | 0.06 |
| | | LEX23 | 0.1 | MPXvgl4-56 | 56 | COR089 | 0.125 |
| | | TKY28 | 0.1 | | | TKY321 | 0.05 |
| MPX-L | 58 | LEX36 | 0.1 | | | LEX69 | 0.125 |
| | | HMS47 | 0.1 | | | LEX52 | 0.05 |
| | | LEX56 | 0.1 | | | A-17 | 0.04 |
| | | COR055 | 0.16 | MPX-R | 58 | UCDEQ457 | 0.1 |
| MPX-M | 58 | ASB1 | 0.1 | | | LEX071 | 0.1 |
| | | COR61 | 0.1 | | | COR033 | 0.1 |
| | | AHT21 | 0.1 | MPX-S | 58 | L12.2 | 0.1 |
| | | COR018 | 0.1 | | | ASB18 | 0.1 |
| MPX-Y | 58 | AHT17 | 0.04 | | | COR065 | 0.1 |
| | | LEX73 | 0.06 | Single Amp | 58 | AHT19 | 0.1 |
| | | COR024 | 0.06 | Single Amp | 58 | COR016 | 0.1 |
| | | COR092 | 0.1 | Single Amp | 58 | COR038 | 0.1 |
| Chrom1 | 58 | ASB41 | 0.12 | Single Amp | 58 | LEX4 | 0.1 |
| | | NVHEQ100 | 0.06 | Single Amp | 58 | LEX38 | 0.1 |
| | | ASB8 | 0.08 | Single Amp | 58 | LEX68 | 0.1 |
| | | HMS15 | 0.08 | Single Amp | 58 | SGCV16 | 0.1 |

Fig. 10

Table 5

| MPX Name | Tm (°C) | Marker | Conc (μM) | MPX Name | Tm (°C) | Marker | Conc (μM) |
|---|---|---|---|---|---|---|---|
| Chr1-A | 58 | HTG12 | 0.2 | Chr1-D | 58 | LEX49 | 1 |
|  |  | UM043 | 0.2 |  |  | 1CA25 | 0.2 |
|  |  | TKY295 | 0.2 | Chr1-E | 58 | UM026 | 0.2 |
| Chr1-B | 58 | AHT58 | 0.2 |  |  | HMS15 | 0.2 |
|  |  | UM004 | 0.2 | Chr1F | 58 | AHT21 | 0.2 |
| Chr1-C | 58 | TKY342 | 0.2 |  |  | ASB8 | 0.2 |
|  |  | UCD440 | 1 |  |  | 1CA43 | 0.2 |

Fig. 11

Table 6

| Locus | Maximum (S) | (E) | Accession | Human Chromosome: MB |
|---|---|---|---|---|
| 1CA25 | 99.6 | 6E-18 | AC06773.1 | HSA15: 75.35 – 75.49 |
| UM043 | 73.8 | 3E-10 | AC129980.6 | HSA15: 71.03 - 71.23 |
| HTG12 | 89.7 | 5E-15 | AC105014.5 | HSA15: 66.65 - 62.77 |
| AHT58 | 163 | 4E-37 | AC090543.12 | HSA15: 62.61 - 62.77 |
| UM004 | 141 | 1E-30 | AC011927.11 | HSA15: 60.55 - 60.68 |
| UCD440 | 266 | 3e-68 | AC009554.14 | HSA15: 59.88 - 60.07 |
| HMS15 | 91.7 | 1E-15 | AC084759.2 | HSA15: 51.91 – 52.07 |
| TKY410 | 222 | 5E-55 | AC016044.11 | HSA15: 50.82 - 50.97 |
| UM026 | 240 | 2E-60 | AC091005.9 | HSA15: 36.00 – 36.15 |

Fig. 12

Table 7

| Primer | Sequence | Application[a] |
|---|---|---|
| CSNK1G1-B | CATTTCCTAGGGCACCATGGA G | |
| PPIB-5UTR-F | TCTTCTCCCGGTGGATGCT | G, I1 |
| PPIB-211-R | GCGAAGAGCACCTTCATGTTCG | |
| PPIB-312-F | TTTGACCTGCGAATTGGAGATG | G, I2 |
| PPIB-388-R | CACTGTTTTTGGAACAGTCTTTCC | G, I1 |
| PPIB-477-F | AGGGTGGAGACTTCACCCGG | G, I3 |
| PPIB-484-R | CCACCCTGGATCATGAAGTCCT | G, I2 |
| PPIB-575-F | GGCTGGGTGAGCATGGCCAA | G, I4, R |
| PPIB-657-R | CTAGCCAGGCTGTCTTCACG | G, I3 |
| PPIB-748-F | CCCTGAAGGATGTGACAA | G |
| PPIB-799-R | GGGCTTCTCCACCTCRATCTT | G, I4, R |
| SNX22-F | AAACGCCTGCCYAACTGG | G |
| Modified Marathon Adapter | CGACTCACTATAGGGCTCGAGC | R |

[a] G = genomic DNA amplification; R = RACE cDNA amplification; I# = Intron x amplification

SEQUENCE LISTING

```
<160> NUMBER OF SEQ ID NOS: 47

<210> SEQ ID NO 1
<211> LENGTH: 6666
<212> TYPE: DNA
<213> ORGANISM: Equus caballus
<220> FEATURE:
<223> OTHER INFORMATION: horse peptidylprolyl isomerase B (PPIB),
      cyclophilin B wild-type genomic sequence
<220> FEATURE:
<221> NAME/KEY: 5'UTR
<222> LOCATION: (1)...(568)
<220> FEATURE:
<221> NAME/KEY: exon
<222> LOCATION: (569)...(717)
<223> OTHER INFORMATION: exon 1
<220> FEATURE:
<221> NAME/KEY: misc_feature
<222> LOCATION: (583)...(585)
<223> OTHER INFORMATION: initiator methionine
<220> FEATURE:
<221> NAME/KEY: intron
```

```
<222> LOCATION: (718)...(1425)
<223> OTHER INFORMATION: intron 1
<220> FEATURE:
<221> NAME/KEY: exon
<222> LOCATION: (1426)...(1539)
<223> OTHER INFORMATION: exon 2
<220> FEATURE:
<221> NAME/KEY: intron
<222> LOCATION: (1540)...(2268)
<223> OTHER INFORMATION: intron 2
<220> FEATURE:
<221> NAME/KEY: exon
<222> LOCATION: (2269)...(2362)
<223> OTHER INFORMATION: exon 3
<220> FEATURE:
<221> NAME/KEY: intron
<222> LOCATION: (2363)...(5387)
<223> OTHER INFORMATION: intron 3
<220> FEATURE:
<221> NAME/KEY: exon
<222> LOCATION: (5388)...(5572)
<223> OTHER INFORMATION: exon 4
<220> FEATURE:
<221> NAME/KEY: intron
<222> LOCATION: (5573)...(6176)
<223> OTHER INFORMATION: intron 4
<220> FEATURE:
<221> NAME/KEY: exon
<222> LOCATION: (6177)...(6497)
<223> OTHER INFORMATION: exon 5
<220> FEATURE:
<221> NAME/KEY: misc_feature
<222> LOCATION: (6297)...(6299)
<223> OTHER INFORMATION: stop codon
<220> FEATURE:
<221> NAME/KEY: 3'UTR
<222> LOCATION: (6498)...(6666)

<400> SEQUENCE: 1
gccttcaatg tggtggattc ggcatatatg tgccctgagt ttttggaagc taccacattt      60
aagtccaatt tggtggtgag taatggttga ctggcccagt gcagacaacg acaagcatct     120
tctgcccata tccacggact tcggcacata agtatcagc caccacctgc caagactccc      180
actcccacaa aggcagggtg ccacgctca gcacgctgag gtctcagcc cctgccgaag       240 cacaaccccc ttgctctgtg aggggcgccg ccttccgcgg atccccttcc tgtgggtggg     300
cctcggcgag ctggggagcc aatcgcgccg cagtaacgtg gcagccatcc acgagcccgc     360
gtctccgccc gcccagtcgg cgagccgggc cccaccccg cggggaccct actattcggc      420
gccgacgcag agggggggaaa tggagcccgc ctcctgccag gaggccggca ggcgccccgg    480
tcccccccgg ccgcactcgg tggcggcgcc ggtgcccacg ccgctgcgcc cccaccctct    540
tccgggcctg ggctgccggg ccgcgctctc ttctcccggt ggatgctgcg tttctcagag    600
cggaacatga aggtgctctt cgccgccgcc ctcatcgtgg gctctgtctt cttcctgctg    660
ttgccaggac cctccacggc cgatgagaag aagaagggc ctaaagtcac tgtcaaggtc    720
tggcctcccc tctccagacc tgcctggcga ggcccgccct ggggtccggc ctcggtgccg    780
ctggtcactg gtgtccgagg ctttacggtc ctaggctggc ttgggctgag cccctcccta    840
gtctccctgc tgtggcttcg tggcgcctgg gcagcctttc cccattctga ccagagaatg    900
acccggacac ctcagccctg acccaggcgc tggagtccgg gatgctcagc tggggccggc    960
gctgtcagcc tcagtgctgt ctgttgcaaa taccctgcag tgctgggaa atggagaga    1020 tcatgtctgc cgatttgcga atgctttctc tacttaggtc aaattttagc cacttccaac    1080
tgcgaggcac agcaataagt ttaaacttgc gtggtgagct taggctttcc tccttatggt    1140
tttttgatgt taatttctag aatctgggcc cattatttgt ttagggcaaa ggttgttacc    1200
```

```
ccgtagtctg aaggagagtg gcaaacaaac atatgggaaa ggggtctgga gctttcatta    1260
gattctcatc gttaggattt ttgtcgccac caaaatcaga ttcagaaaca ttgctttaa    1320 aatatggctc ttttctctcc catcctcagg gtagcttctt gggccctgcc ttgcctagca    1380
aggcccattt aaagaggcta agtttgaaat ggcctttttc ctcaggtgta ctttgacctg    1440
cgaattggag atgaagatat aggccgggtg gtcatcggtc tctttggaaa gactgttcca    1500
aaaacagtgg ataattttgt ggccttagct acaggagagg taagtggctg cagcagaggt    1560
aggcaaactc agatgaagcg aagaaccagt cgggctggca gcaaaccgaa gagcagagcg    1620
cagtccatct atagcagtag ccctcactgg gtaccagcta actgttgccc tgtggcactg    1680
ggaaccaagt attatcttat cttctaagtt ttttaaactg aatccagaaa tctggatttt    1740
tttttttttt ttttggagaa aacttttcat cttttaagac attgtgataa ccaaagaaaa    1800
tatatctgtg gaaattagtt tttggcttct gtgccaaagc tttctcttaa gagtaagggc    1860
ccagagcttc ccaggtttta agaaaacaag ggtgccccat tttaaaaagt ttgtattcca    1920 acttttatt aggtcagcag gtaactttt ttttggtcag ttttcttgaa tcttttctta    1980
tgattatgaa aaaagagaa ggtggaggca ttctgtgaag taaaatcgta caaagtctgg    2040
cacttgtgta aaggcagagg aacgtgcagt cttagcccgt cttggggctg tgcactccat    2100
gcctggccta cagcggtggc ttgcccggag cacgttgaac gataattctg ccagcagca    2160 gtgtctcttc tgtgagcacg actggttgtg ggctgggttc ctgcagggcc tgtttaatgt    2220
ctgcctggtg cttcatgcca cttcctcacc ttctcatccc ttttctagaa aggatttggc    2280
tacaaagaca gcaaattcca tcgtgtgatc aaggacttca tgatccaggg tggagacttc    2340
acccggggag atggcactgg aggtaacctc agtcctctgg gcagaggggt ctgtcagtgc    2400
agcctccaag gtgggagggc ctggctgtgt tgggtagatg aggcctcttc cttcctcagc    2460
tccaggggca ggcctgttaa ccttcattga gaccagctgc acccttcttt gtatgggaa    2520 cccaggacaa aggagaggga gtaatggggg gtcaggtgga cataagagga tctcgcttag    2580
ctggcagagc tgctgatcca ggcctatagc cttggtgact tttcttgcaa taatacctcc    2640
tggagggagg ggagcaagtg aaacacaggg gtgggtcagg catgcaaagc ctgtgtgggg    2700
cgacctttga agccccagca aaggtgggag aagttgcttt ccttggcagt ttcccaccag    2760
cgaccactta gcgagagctg actgtcttgc ctctgcatta cttgtacaca taggacagac    2820
agacagatac cctggactaa ctaacccaca ggtctcgcca tactttggtg cacagcctac    2880
tgtcccctcg gaccacagat tcagctaacc ccatcaatga atattcattg ccagactct    2940 ggtgggtgct gaggacacaa aaatcagtgg aacagcaact cccttcact tcccaatacc    3000 tgaaaactca cacatgggcg gtaatacagc ttttaggact caggctctgt cctcaagttg    3060
tttatcattt aggtgggaaa aactaggaga aaacactctg aaaattatat aacaagacaa    3120
gatttaagtg gtagctagtg gcaacagtgg atggggaagg acgcatgtaa tcatggagtc    3180
agatacagtt gggtgtaacc tagtgtctgc caccttcttg ctttgtgacc tcaggacctc    3240
tgagctttgg tttcctcttc tgtaaagtga gagcggcaag agttgtgggt gctgtgaggg    3300
gtaggtgaga tcctgagtgt taagagccca catatggtga gggaagtcag ccgttgtcga    3360
agtgccgaca agcagaggat ctgtttcagg ccacggtggt caggaaacgg ccttgtgaac    3420
atgacgaaag atgtgcgtca ggtcctggct ggaagaattt gggcaaagag gaggcaaggt    3480
taaggtgtga gcccagctct gttctgtggc aggagcttgg ccaaaggtgg ggctgaagga    3540
```

```
atggaagtgg agcacacccc aggagccagg agtggtgggc tgcagcctga cctggggacc    3600
agggctttgt cctacatgga gtgaggatcc actgaagact tgagtggagg aagacccaat    3660
cacacaggag tttgagggaa ataatgtgg caacaggatt caggatgtgg aggcaggagc     3720
aagtggatgg gtgaggtacc agtgtggctg tccctgttag gaccacgtgg gcctgagccc    3780
caggagacga tagcctagtg ggtaaaggca gagacttgag aggcagacca ccttggtttg    3840
aattccagct ctgctccttc ctagctgggg gaccgtgaag ctctctgtac ctcagtttct    3900
tcgtctttga ataaggtca ttagctcctg cctcccaggg tgggttcttc tgtgtgtaaa     3960
atgcttgcag cagttctctg gcacccgccg ttaccacact aagcatcagc ccttgttgca    4020
gtggggtagc aggaatggaa agaaaggatg gggctgcgga cgacaacaat gtgcagagga    4080
aaagctgtca gaagaataac tgaagtctgg agggaaagat gacttactct gctgagttta    4140
aaatgaactg tctgttcaag tttggaactc ctttgtcttg ggaaagtgat tggagctaag    4200
gatgtagatt tggggatttt tctggttagc ggcaataact gaaaccctgc agttggttga    4260
gattcacaac gaggattctc acacagggga ggcgtttagc cagcaccca gccaggagtc     4320
actgcacgat gctgggagag tccggttttt ccctggggta ggagtgagac ggggagcaca    4380
ggctgacaca ccccagcccc caccagccag agtccagtaa ttcttggttt tccgtctccc    4440
cacttgctac acaaccagaa atttctccct gattagcatc agtctaggac agtatcccaa    4500
cctggttcca ttctgtggaa ccacaggatg aaaacagttc tatcaaggag gaaaaaggg    4560
tttcatgtgc aagtaagttt gaaggtgct gggtaaaaca aaatgaaaat tgcttctttc    4620
ttgctgggtt tctcggggcc cctagttcac tagcgcagtg tgaatcccg aggggggcagg   4680
gaaaaagaag ggtgtgctgt ttctcctgga acagcgctgg gaacttaggt taggctctct    4740
gaagtggcgt cgaggtctgc tttcggcccc ctttgtcacg cgccccagcg ctcagggaca    4800
gttacatcac agacggtcac agccaccttt tattttctgt tcatttgttc ataagaggct    4860
cctgacttgc cagaacccaa atggcagccc ctctcttgct tctccctgcc ccgcccactc    4920
atctctcggc tttctgtgtt gcagacacct cagcgtcttt tgtgctcgta agaaaagctg    4980
gtcagccaca gcagttctcc ttttctggag cgttcttagc gcccctgccc cctgcatcct    5040
gcacagcacc tcttcaccag agttccccca tggcaggcct ctcaggccat aatagccaag    5100
ggtagctgtt aatatgtgcc ttatttaaaa gccgtaaaac tatattctga agaaatcca    5160
ttgtgtgagc ttctcattag atcagcttgg cctcatgctg ccacacttgg tcagcatggt    5220
ttggctccaa ggccagaggg tcagaaggga cagcttttat gttcttgtac tccacttgag    5280
cctggcctgg cacagaggac ggacaggttg agccctgga atcctcaccc caaagatctg     5340
ctcggttgt gccagcccag ctcccctgac ccactctttc ttcccaggta agagcatcta     5400
cggtgaacgc ttcccagacg agaacttcaa gctgaaacac tatgggcccg gctgggtgag    5460
catgccaac gcaggcaaag acaccaacgg ctcccagttc tttatcacga ccgtgaagac     5520
agcctggcta gatggcaagc acgtagtgtt cggcaaagtt ctagagggca tggtgagttc    5580
ggaggaaggg gctaaacctg ggtgcccctc accaaggatc tgacacagac cctggggcag    5640
gagctccata tattttatcc ccttccaaaa ggaaaaccca cagattcaga ccattgttca    5700
tctttacaga cctgggggaa tggagaataa atagcctacc tctctatgcc cacaagttct    5760
aaatcctttc aggcccaggc agaagctggc cagggcttat tgtggctccg tccatcactg    5820
actcagtgac atgcggcacc accctaagtt gtacagggca cagctgaaca cgatgtccct    5880
gagaagccat ttggtacccc ttccccagcc acccccttcc tccctctcac ccatagccca    5940
```

```
acctgggtca tacttcaaag ggtcaagact gctccatcct cttgtcagag ctgggttctt    6000
ccttccctgg gctggcccct ggccatgatt ccgttaggat tttggtgcct caaggcttgt    6060
atgctgcttg tcacatgggg gtctcagccc tccccagcca tacactgggg cctgcctctc    6120
ttgagtggct gcctcctgac ccactctgcc ttcctgcttc tgcctttcct tcccaggagg    6180
tagtgcggaa ggtggagacc accaagacag atgggcgcga caagcccctg aaggatgtga    6240
caattgcaga ctgtggcaag atcgaggtgg agaagccctt tgccatcgcc aaggagtagg    6300
gcctggggac ttcctccctt tgagcaacca tctgtgcagc cgtgttgccc ccaaggggt     6360 gaagacagcc tgccacaggg ctctgcgctc ccactggccc cagtggtggc atctgacgga    6420
gtggactcct cccctcacat tccacagggc ccagttttgt aacaaactcc taccaacact    6480
gaccaataaa agaaaaggt gggttttta taacctgtgt gtgggctcgg ttcttgggcc      6540
tgcagcacct cccctcagt ctgtgtcccg gtgtgcctgg acctgtggc agcgggtgct      6600 gtcccctctg tggactctgg cctgaaccca ttccccagat gctacataca aacatcaag     6660 cagggg                                                              6666

<210> SEQ ID NO 2
<211> LENGTH: 651
<212> TYPE: DNA
<213> ORGANISM: Equus caballus
<220> FEATURE:
<223> OTHER INFORMATION: horse peptidylprolyl isomerase B (PPIB),
      cyclophilin B hereditary equine regional dermal
      asthenia (HERDA) or hyperelastosis cutis allele cDNA

<400> SEQUENCE: 2
atgctgcgtt tctcagggcg gaacatgaag gtgctcttcg ccgccgccct catcgtgggc     60
tctgtcttct tcctgctgtt gccaggaccc tccacggccg atgagaagaa gaagaggcct    120
aaagtcactg tcaaggtgta ctttgacctg cgaattggag atgaagatat aggccgggtg    180
gtcatcggtc tctttggaaa gactgttcca aaaacagtgg ataattttgt ggccttagct    240
acaggagaga aaggatttgg ctacaaagac agcaaattcc atcgtgtgat caaggacttc    300
atgatccagg gtggagactt cacccgggga gatggcactg gaggtaagag catctacggt    360
gaacgcttcc cagacgagaa cttcaagctg aaacactatg gcccggctg gtgagcatg      420 gccaacgcag gcaaagacac caacggctcc cagttctta tcacgaccgt gaagacagcc     480
tggctagatg gcaagcacgt agtgttcggc aaagttctag agggcatgga ggtagtgcgg    540
aaggtggaga ccaccaagac agatgggcgc gacaagcccc tgaaggatgt gacaattgca    600
gactgtggca gatcgaggt ggagaagccc tttgccatcg ccaaggagta g              651

<210> SEQ ID NO 3
<211> LENGTH: 651
<212> TYPE: DNA
<213> ORGANISM: Equus caballus
<220> FEATURE:
<223> OTHER INFORMATION: horse peptidylprolyl isomerase B (PPIB),
      cyclophilin B wild type cDNA

<400> SEQUENCE: 3
atgctgcgtt tctcagagcg gaacatgaag gtgctcttcg ccgccgccct catcgtgggc     60
tctgtcttct tcctgctgtt gccaggaccc tccacggccg atgagaagaa gaaggggcct    120
aaagtcactg tcaaggtgta ctttgacctg cgaattggag atgaagatat aggccgggtg    180
gtcatcggtc tctttggaaa gactgttcca aaaacagtgg ataattttgt ggccttagct    240
```

```
acaggagaga aaggatttgg ctacaaagac agcaaattcc atcgtgtgat caaggacttc    300
atgatccagg gtggagactt cacccgggga gatggcactg gaggtaagag catctacggt    360
gaacgcttcc cagacgagaa cttcaagctg aaacactatg gcccggctg ggtgagcatg     420 gccaacgcag gcaaagacac caacggctcc cagttcttta tcacgaccgt gaagacagcc    480
tggctagatg gcaagcacgt agtgttcggc aaagttctag agggcatgga ggtagtgcgg    540
aaggtggaga ccaccaagac agatgggcgc gacaagcccc tgaaggatgt gacaattgca    600
gactgtggca agatcgaggt ggagaagccc tttgccatcg ccaaggagta g             651
```

<210> SEQ ID NO 4
<211> LENGTH: 19
<212> TYPE: DNA
<213> ORGANISM: Artificial Sequence
<220> FEATURE:
<223> OTHER INFORMATION: synthetic SNP2 (PPIB*HRD) PCR amplification
      forward primer

<400> SEQUENCE: 4

```
cggtggatgc tgcgtttct                                                  19
```

<210> SEQ ID NO 5
<211> LENGTH: 18
<212> TYPE: DNA
<213> ORGANISM: Artificial Sequence
<220> FEATURE:
<223> OTHER INFORMATION: synthetic SNP2 (PPIB*HRD) PCR amplification
      reverse primer
<220> FEATURE:
<221> NAME/KEY: modified_base
<222> LOCATION: (1)...(1)
<223> OTHER INFORMATION: g modified by 6FAM fluorescent label

<400> SEQUENCE: 5

```
gcccaagcca gcctagga                                                   18
```

<210> SEQ ID NO 6
<211> LENGTH: 100
<212> TYPE: PRT
<213> ORGANISM: Equus caballus
<220> FEATURE:
<223> OTHER INFORMATION: first 100 residues of horse peptidylprolyl
      isomerase B (PPIB), cyclophilin B hereditary
      equine regional dermal asthenia (HERDA) or
      hyperelastosis cutis allele

<400> SEQUENCE: 6

```
Met Leu Arg Phe Ser Gly Arg Asn Met Lys Val Leu Phe Ala Ala
1               5                   10                  15

Leu Ile Val Gly Ser Val Phe Phe Leu Leu Pro Gly Pro Ser Thr
                20                  25                  30

Ala Asp Glu Lys Lys Lys Arg Pro Lys Val Thr Val Lys Val Tyr Phe
            35                  40                  45

Asp Leu Arg Ile Gly Asp Glu Asp Ile Gly Arg Val Val Ile Gly Leu
        50                  55                  60

Phe Gly Lys Thr Val Pro Lys Thr Val Asp Asn Phe Val Ala Leu Ala
65                  70                  75                  80

Thr Gly Glu Lys Gly Phe Gly Tyr Lys Asp Ser Lys Phe His Arg Val
                85                  90                  95

Ile Lys Asp Phe
            100
```

<210> SEQ ID NO 7
<211> LENGTH: 100
<212> TYPE: PRT
<213> ORGANISM: Equus caballus
<220> FEATURE:
<223> OTHER INFORMATION: first 100 residues of horse peptidylprolyl
      isomerase B (PPIB), cyclophilin B wild-type allele

<400> SEQUENCE: 7

Met Leu Arg Phe Ser Glu Arg Asn Met Lys Val Leu Phe Ala Ala Ala
1               5                   10                  15

Leu Ile Val Gly Ser Val Phe Phe Leu Leu Pro Gly Pro Ser Thr
                20                  25                  30

Ala Asp Glu Lys Lys Lys Gly Pro Lys Val Thr Val Lys Val Tyr Phe
            35                  40                  45

Asp Leu Arg Ile Gly Asp Glu Asp Ile Gly Arg Val Val Ile Gly Leu
        50                  55                  60

Phe Gly Lys Thr Val Pro Lys Thr Val Asp Asn Phe Val Ala Leu Ala
65                  70                  75                  80

Thr Gly Glu Lys Gly Phe Gly Tyr Lys Asp Ser Lys Phe His Arg Val
                85                  90                  95

Ile Lys Asp Phe
            100

<210> SEQ ID NO 8
<211> LENGTH: 100
<212> TYPE: PRT
<213> ORGANISM: Canis familiaris
<220> FEATURE:
<223> OTHER INFORMATION: first 100 residues of dog peptidylprolyl isomerase
      B (PPIB), cyclophilin B

<400> SEQUENCE: 8

Met Leu Arg Leu Ser Glu Arg Asn Met Lys Val Leu Phe Ala Ala Ala
1               5                   10                  15

Leu Val Val Gly Ser Val Phe Phe Leu Leu Pro Gly Pro Ser Thr
                20                  25                  30

Ala Asp Glu Lys Lys Lys Gly Pro Lys Val Thr Val Lys Val Tyr Phe
            35                  40                  45

Asp Leu Arg Ile Gly Asp Glu Asp Ile Gly Arg Val Val Ile Gly Leu
        50                  55                  60

Phe Gly Lys Thr Val Pro Lys Thr Val Asp Asn Phe Val Ala Leu Ala
65                  70                  75                  80

Thr Gly Glu Lys Gly Phe Gly Tyr Lys Asp Ser Lys Phe His Arg Val
                85                  90                  95

Ile Lys Asp Phe
            100

<210> SEQ ID NO 9
<211> LENGTH: 100
<212> TYPE: PRT
<213> ORGANISM: Bos taurus
<220> FEATURE:
<223> OTHER INFORMATION: first 100 residues of bovine peptidylprolyl isomerase
      B (PPIB), cyclophilin B

<400> SEQUENCE: 9

Met Leu Arg Leu Ser Glu Arg Asn Met Lys Ile Leu Phe Val Ala Ala
1               5                   10                  15

Leu Val Val Gly Ser Val Phe Phe Leu Leu Leu Pro Gly Pro Ser Ala

```
                20                  25                  30

Ala Asp Glu Lys Lys Lys Gly Pro Lys Val Thr Val Lys Val Tyr Phe
        35                  40                  45

Asp Leu Arg Ile Gly Asp Glu Asp Ile Gly Arg Val Val Ile Gly Leu
    50                  55                  60

Phe Gly Lys Thr Val Pro Lys Thr Val Asp Asn Phe Val Ala Leu Ala
 65                 70                  75                  80

Thr Gly Glu Lys Gly Phe Gly Tyr Lys Asp Ser Lys Phe His Arg Val
                85                  90                  95

Ile Lys Asp Phe
            100

<210> SEQ ID NO 10
<211> LENGTH: 100
<212> TYPE: PRT
<213> ORGANISM: Homo sapiens
<220> FEATURE:
<223> OTHER INFORMATION: first 100 residues of human peptidylprolyl
      isomerase B (PPIB), cyclophilin B

<400> SEQUENCE: 10

Met Leu Arg Leu Ser Glu Arg Asn Met Lys Val Leu Leu Ala Ala Ala
 1               5                  10                  15

Leu Ile Ala Gly Ser Val Phe Phe Leu Leu Pro Gly Pro Ser Ala
            20                  25                  30

Ala Asp Glu Lys Lys Lys Gly Pro Lys Val Thr Val Lys Val Tyr Phe
        35                  40                  45

Asp Leu Arg Ile Gly Asp Glu Asp Val Gly Arg Val Ile Phe Gly Leu
    50                  55                  60

Phe Gly Lys Thr Val Pro Lys Thr Val Asp Asn Phe Val Ala Leu Ala
 65                 70                  75                  80

Thr Gly Glu Lys Gly Phe Gly Tyr Lys Asn Ser Lys Phe His Arg Val
                85                  90                  95

Ile Lys Asp Phe
            100

<210> SEQ ID NO 11
<211> LENGTH: 100
<212> TYPE: PRT
<213> ORGANISM: Mus musculus
<220> FEATURE:
<223> OTHER INFORMATION: first 100 residues of mouse peptidylprolyl
      isomerase B (PPIB), cyclophilin B

<400> SEQUENCE: 11

Met Leu Arg Leu Ser Glu Arg Asn Met Lys Val Leu Phe Ala Ala Ala
 1               5                  10                  15

Leu Ile Val Gly Ser Val Val Phe Leu Leu Pro Gly Pro Ser Val
            20                  25                  30

Ala Asn Asp Lys Lys Lys Gly Pro Lys Val Thr Val Lys Val Tyr Phe
        35                  40                  45

Asp Leu Gln Ile Gly Asp Glu Ser Val Gly Arg Val Val Phe Gly Leu
    50                  55                  60

Phe Gly Lys Thr Val Pro Lys Thr Val Asp Asn Phe Val Ala Leu Ala
 65                 70                  75                  80

Thr Gly Glu Lys Gly Phe Gly Tyr Lys Asn Ser Lys Phe His Arg Val
                85                  90                  95

Ile Lys Asp Phe
```

```
                                   100

<210> SEQ ID NO 12
<211> LENGTH: 100
<212> TYPE: PRT
<213> ORGANISM: Rattus norvegicus
<220> FEATURE:
<223> OTHER INFORMATION: first 100 residues of rat peptidylprolyl isomerase
      B (PPIB), cyclophilin B

<400> SEQUENCE: 12

Met Leu Arg Leu Ser Glu Arg Asn Met Lys Val Leu Phe Ala Ala Ala
1               5                   10                  15

Leu Ile Val Gly Ser Val Val Phe Leu Leu Pro Gly Pro Ser Val
            20                  25                  30

Ala Asn Asp Lys Lys Gly Pro Lys Val Thr Val Lys Val Tyr Phe
        35                  40                  45

Asp Phe Gln Ile Gly Asp Glu Pro Val Gly Arg Val Thr Phe Gly Leu
    50                  55                  60

Phe Gly Lys Thr Val Pro Lys Thr Val Asp Asn Phe Val Ala Leu Ala
65                  70                  75                  80

Thr Gly Glu Lys Gly Phe Gly Tyr Lys Asn Ser Lys Phe His Arg Val
                85                  90                  95

Ile Lys Asp Phe
            100

<210> SEQ ID NO 13
<211> LENGTH: 100
<212> TYPE: PRT
<213> ORGANISM: Danio rerio
<220> FEATURE:
<223> OTHER INFORMATION: first 100 residues of zebrafish peptidylprolyl
      isomerase B (PPIB), cyclophilin B

<400> SEQUENCE: 13

Met Val Arg Ile Cys Glu Arg Arg Met Lys Phe Leu Val Ala Val Thr
1               5                   10                  15

Leu Ile Val Gly Ser Val Val Phe Leu Leu Phe Pro Ser Glu Thr Glu
            20                  25                  30

Ala Asp Glu Lys Lys Lys Gly Pro Lys Val Thr Ala Lys Val Tyr Phe
        35                  40                  45

Asp Ile Lys Ile Gly Asp Glu Asp Ala Gly Arg Ile Val Ile Gly Leu
    50                  55                  60

Phe Gly Lys Thr Val Pro Lys Thr Thr Glu Asn Phe Leu Gln Leu Ala
65                  70                  75                  80

Thr Gly Glu Lys Gly Phe Gly Tyr Lys Gly Ser Lys Phe His Arg Val
                85                  90                  95

Ile Lys Asp Phe
            100

<210> SEQ ID NO 14
<211> LENGTH: 92
<212> TYPE: PRT
<213> ORGANISM: Xenopus tropicalis
<220> FEATURE:
<223> OTHER INFORMATION: first 92 residues of Western clawed frog
      peptidylprolyl isomerase B (PPIB), cyclophilin B

<400> SEQUENCE: 14

Met Lys Leu Leu Val Ala Ala Ala Leu Ile Ala Gly Ser Val Ile Phe
1               5                   10                  15
```

Leu Leu Phe Pro Gly Ser Ser Val Ala Asp Glu Lys Lys Gly Pro
            20                  25                  30

Lys Val Thr His Lys Val Tyr Phe Asp Ile Lys Ile Gly Asp Glu Asp
        35                  40                  45

Val Gly Arg Val Val Ile Gly Leu Phe Gly Lys Thr Val Pro Lys Thr
    50                  55                  60

Val Glu Asn Phe Val Thr Leu Ala Thr Gly Glu Lys Gly Phe Gly Tyr
65                  70                  75                  80

Lys Gly Ser Lys Phe His Arg Val Ile Lys Asp Phe
                85                  90

<210> SEQ ID NO 15
<211> LENGTH: 91
<212> TYPE: PRT
<213> ORGANISM: Gallus gallus
<220> FEATURE:
<223> OTHER INFORMATION: first 91 residues of chicken peptidylprolyl
      isomerase B (PPIB), cyclophilin B

<400> SEQUENCE: 15

Met Lys Ala Leu Val Ala Ala Thr Ala Leu Gly Pro Ala Leu Leu Leu
1               5                   10                  15

Leu Leu Pro Ala Ala Ser Arg Ala Asp Glu Arg Lys Lys Gly Pro Lys
            20                  25                  30

Val Thr Ala Lys Val Phe Phe Asp Leu Arg Val Gly Glu Glu Asp Ala
        35                  40                  45

Gly Arg Val Val Ile Gly Leu Phe Gly Lys Thr Val Pro Lys Thr Val
    50                  55                  60

Glu Asn Phe Val Ala Leu Ala Thr Gly Glu Lys Gly Phe Gly Phe Lys
65                  70                  75                  80

Gly Ser Lys Phe His Arg Val Ile Lys Asp Phe
                85                  90

<210> SEQ ID NO 16
<211> LENGTH: 19
<212> TYPE: DNA
<213> ORGANISM: Artificial Sequence
<220> FEATURE:
<223> OTHER INFORMATION: synthetic ITGA11 PCR amplification forward
      primer

<400> SEQUENCE: 16
acctgtcttc ctggcgccc                                            19

<210> SEQ ID NO 17
<211> LENGTH: 22
<212> TYPE: DNA
<213> ORGANISM: Artificial Sequence
<220> FEATURE:
<223> OTHER INFORMATION: synthetic ITGA11 PCR amplification reverse
      primer

<400> SEQUENCE: 17
cagcacatgg aagttgatcc ga                                        22

<210> SEQ ID NO 18
<211> LENGTH: 15
<212> TYPE: DNA
<213> ORGANISM: Artificial Sequence
<220> FEATURE:
<223> OTHER INFORMATION: ITGA11 control single nucleotide polymorphism
      (SNP) with flanking sequence

<400> SEQUENCE: 18
cggtccccgc cctca          15

<210> SEQ ID NO 19
<211> LENGTH: 15
<212> TYPE: DNA
<213> ORGANISM: Artificial Sequence
<220> FEATURE:
<223> OTHER INFORMATION: ITGA11 HRDA single nucleotide polymorphism
      (SNP) with flanking sequence

<400> SEQUENCE: 19
cggtcccagc cctca          15

<210> SEQ ID NO 20
<211> LENGTH: 21
<212> TYPE: DNA
<213> ORGANISM: Artificial Sequence
<220> FEATURE:
<223> OTHER INFORMATION: synthetic cartilage intermediate layer protein
      (CILP) PCR amplification forward primer

<400> SEQUENCE: 20
tggtgcctca acagggagca g          21

<210> SEQ ID NO 21
<211> LENGTH: 20
<212> TYPE: DNA
<213> ORGANISM: Artificial Sequence
<220> FEATURE:
<223> OTHER INFORMATION: synthetic cartilage intermediate layer protein
      (CILP) PCR amplification reverse primer

<400> SEQUENCE: 21
cacttgctcc agggagacca          20

<210> SEQ ID NO 22
<211> LENGTH: 15
<212> TYPE: DNA
<213> ORGANISM: Artificial Sequence
<220> FEATURE:
<223> OTHER INFORMATION: cartilage intermediate layer protein (CILP)
      control single nucleotide polymorphism (SNP) with
      flanking sequence

<400> SEQUENCE: 22
agacagggtt tatgt          15

<210> SEQ ID NO 23
<211> LENGTH: 15
<212> TYPE: DNA
<213> ORGANISM: Artificial Sequence
<220> FEATURE:
<223> OTHER INFORMATION: cartilage intermediate layer protein (CILP)
      HRDA single nucleotide polymorphism (SNP) with flanking
      sequence

<400> SEQUENCE: 23
agacaggatt tatgt          15

<210> SEQ ID NO 24
<211> LENGTH: 22
<212> TYPE: DNA
<213> ORGANISM: Artificial Sequence
<220> FEATURE:
<223> OTHER INFORMATION: synthetic SPG21 PCR amplification fluorescently labled forward primer
<220> FEATURE:
<221> NAME/KEY: modified_base
<222> LOCATION: (1)...(1)
<223> OTHER INFORMATION: t modified by VIC fluorescent label

<400> SEQUENCE: 24
tcatactctg accccgctga tc                                              22

<210> SEQ ID NO 25
<211> LENGTH: 23
<212> TYPE: DNA
<213> ORGANISM: Artificial Sequence
<220> FEATURE:
<223> OTHER INFORMATION: synthetic SPG21 PCR amplification reverse
      primer

<400> SEQUENCE: 25
tttaattttc cttcccactc acg                                             23

<210> SEQ ID NO 26
<211> LENGTH: 23
<212> TYPE: DNA
<213> ORGANISM: Artificial Sequence
<220> FEATURE:
<223> OTHER INFORMATION: synthetic USP3 PCR amplification forward primer

<400> SEQUENCE: 26
agctttcaca gctgacaggc ata                                             23

<210> SEQ ID NO 27
<211> LENGTH: 23
<212> TYPE: DNA
<213> ORGANISM: Artificial Sequence
<220> FEATURE:
<223> OTHER INFORMATION: synthetic USP3 PCR amplification reverse primer

<400> SEQUENCE: 27
tgagtgactg aaggatggca ttc                                             23

<210> SEQ ID NO 28
<211> LENGTH: 15
<212> TYPE: DNA
<213> ORGANISM: Artificial Sequence
<220> FEATURE:
<223> OTHER INFORMATION: USP3 control single nucleotide polymorphism
      (SNP) with flanking sequence

<400> SEQUENCE: 28
aacacccact catgt                                                      15

<210> SEQ ID NO 29
<211> LENGTH: 15
<212> TYPE: DNA
<213> ORGANISM: Artificial Sequence
<220> FEATURE:
<223> OTHER INFORMATION: USP3 HRDA single nucleotide polymorphism (SNP)
      with flanking sequence

<400> SEQUENCE: 29
aacacccgct catgt                                                      15

<210> SEQ ID NO 30
<211> LENGTH: 24
<212> TYPE: DNA
<213> ORGANISM: Artificial Sequence
<220> FEATURE:

<223> OTHER INFORMATION: synthetic TLN2 PCR amplification forward primer

<400> SEQUENCE: 30
ctcgtcagaa aatcagtact tctc                                          24

<210> SEQ ID NO 31
<211> LENGTH: 20
<212> TYPE: DNA
<213> ORGANISM: Artificial Sequence
<220> FEATURE:
<223> OTHER INFORMATION: synthetic TLN2 PCR amplification reverse primer

<400> SEQUENCE: 31
ccaatcccca ccccaagata                                               20

<210> SEQ ID NO 32
<211> LENGTH: 15
<212> TYPE: DNA
<213> ORGANISM: Artificial Sequence
<220> FEATURE:
<223> OTHER INFORMATION: TLN2 control single nucleotide polymorphism
      (SNP) with flanking sequence

<400> SEQUENCE: 32
ggagaaccca caagc                                                    15

<210> SEQ ID NO 33
<211> LENGTH: 15
<212> TYPE: DNA
<213> ORGANISM: Artificial Sequence
<220> FEATURE:
<223> OTHER INFORMATION: TLN2 HRDA single nucleotide polymorphism (SNP)
      with flanking sequence

<400> SEQUENCE: 33
ggagaactca caagc                                                    15

<210> SEQ ID NO 34
<211> LENGTH: 21
<212> TYPE: DNA
<213> ORGANISM: Artificial Sequence
<220> FEATURE:
<223> OTHER INFORMATION: synthetic CSNK1G1-B PCR amplification primer

<400> SEQUENCE: 34
catttcctag ggcaccatgg a                                             21

<210> SEQ ID NO 35
<211> LENGTH: 19
<212> TYPE: DNA
<213> ORGANISM: Artificial Sequence
<220> FEATURE:
<223> OTHER INFORMATION: synthetic PPIB-5UTR-F PCR amplification forward
      primer for genomic DNA amplification and intron 1
      amplification

<400> SEQUENCE: 35
tcttctcccg gtggatgct                                                19

<210> SEQ ID NO 36
<211> LENGTH: 21
<212> TYPE: DNA
<213> ORGANISM: Artificial Sequence
<220> FEATURE:
<223> OTHER INFORMATION: synthetic PPIB-211-R PCR amplification reverse
      primer

```
<400> SEQUENCE: 36
gcgaagagca ccttcatgtt c                                               21

<210> SEQ ID NO 37
<211> LENGTH: 22
<212> TYPE: DNA
<213> ORGANISM: Artificial Sequence
<220> FEATURE:
<223> OTHER INFORMATION: synthetic PPIB-312-F PCR amplification forward
      primer for genomic DNA amplification and intron 2
      amplification

<400> SEQUENCE: 37
tttgacctgc gaattggaga tg                                              22

<210> SEQ ID NO 38
<211> LENGTH: 24
<212> TYPE: DNA
<213> ORGANISM: Artificial Sequence
<220> FEATURE:
<223> OTHER INFORMATION: synthetic PPIB-388-R PCR amplification reverse
      primer for genomic DNA amplification and intron 1
      amplification

<400> SEQUENCE: 38
cactgttttt ggaacagtct ttcc                                            24

<210> SEQ ID NO 39
<211> LENGTH: 20
<212> TYPE: DNA
<213> ORGANISM: Artificial Sequence
<220> FEATURE:
<223> OTHER INFORMATION: synthetic PPIB-477-F PCR amplification forward
      primer for genomic DNA amplification and intron 3
      amplification

<400> SEQUENCE: 39
agggtggaga cttcacccgg                                                 20

<210> SEQ ID NO 40
<211> LENGTH: 22
<212> TYPE: DNA
<213> ORGANISM: Artificial Sequence
<220> FEATURE:
<223> OTHER INFORMATION: synthetic PPIB-484-R PCR amplification reverse
      primer for genomic DNA amplification and intron 2
      amplification

<400> SEQUENCE: 40
ccaccctgga tcatgaagtc ct                                              22

<210> SEQ ID NO 41
<211> LENGTH: 20
<212> TYPE: DNA
<213> ORGANISM: Artificial Sequence
<220> FEATURE:
<223> OTHER INFORMATION: synthetic PPIB-575-F PCR amplification forward
      primer for genomic DNA amplification and intron 4
      amplification and RACE cDNA amplification

<400> SEQUENCE: 41
ggctgggtga gcatggccaa                                                 20

<210> SEQ ID NO 42
<211> LENGTH: 20
<212> TYPE: DNA
<213> ORGANISM: Artificial Sequence
```

```
<220> FEATURE:
<223> OTHER INFORMATION: synthetic PPIB-657-R PCR amplification reverse
      primer for genomic DNA amplification and intron 3
      amplification

<400> SEQUENCE: 42
ctagccaggc tgtcttcacg                                                   20

<210> SEQ ID NO 43
<211> LENGTH: 18
<212> TYPE: DNA
<213> ORGANISM: Artificial Sequence
<220> FEATURE:
<223> OTHER INFORMATION: synthetic PPIB-748-F PCR amplification forward
      primer for genomic DNA amplification

<400> SEQUENCE: 43
ccctgaagga tgtgacaa                                                     18

<210> SEQ ID NO 44
<211> LENGTH: 21
<212> TYPE: DNA
<213> ORGANISM: Artificial Sequence
<220> FEATURE:
<223> OTHER INFORMATION: synthetic PPIB-799-R PCR amplification reverse
      primer for genomic DNA amplification and intron 4
      amplification and RACE cDNA amplification

<400> SEQUENCE: 44
gggcttctcc acctcratct t                                                 21

<210> SEQ ID NO 45
<211> LENGTH: 18
<212> TYPE: DNA
<213> ORGANISM: Artificial Sequence
<220> FEATURE:
<223> OTHER INFORMATION: synthetic SNX22-F PCR amplification forward
      primer for genomic DNA amplification

<400> SEQUENCE: 45
aaacgcctgc cyaactgg                                                     18

<210> SEQ ID NO 46
<211> LENGTH: 22
<212> TYPE: DNA
<213> ORGANISM: Artificial Sequence
<220> FEATURE:
<223> OTHER INFORMATION: synthetic Modified Marathon Adapter PCR
      amplification forward primer for RACE cDNA
      amplification

<400> SEQUENCE: 46
cgactcacta tagggctcga gc                                                22

<210> SEQ ID NO 47
<211> LENGTH: 7
<212> TYPE: PRT
<213> ORGANISM: Artificial Sequence
<220> FEATURE:
<223> OTHER INFORMATION: conserved PPIB seven amino acid peptide

<400> SEQUENCE: 47

Lys Lys Gly Pro Lys Val Thr
1               5
```

METHODS FOR DETECTING A CYCLOPHILIN B SNP ASSOCIATED WITH HERDA

CROSS-REFERENCES TO RELATED APPLICATIONS

This application claims the benefit of U.S. Provisional Patent Application No. 60/826,038, filed Sep. 18, 2006, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Hereditary equine regional dermal asthenia (HERDA) is an inherited skin disease predominantly found in the American Quarter Horse. The classic phenotype of velvety hyperextensible skin, accompanied with seromas and hematomas particularly along the dorsal aspect, does not normally present until sometime after 6 months of age, often as old as two years when the horse is first being broke to saddle. The inability to treat the disease most commonly results in euthanasia of the affected horse. While there have been relatively few HERDA (historically, also referred to as hyperelastosis cutis) cases reported throughout the past thirty years, an increase in the incidence of HERDA cases being seen by veterinary dermatologists occurred in the late 1990's.

Pedigree analysis suggests an autosomal recessive mode of inheritance, with a common ancestor that can be traced back via both the paternal and maternal lines in all HERDA cases with complete pedigrees. Heritability analysis corroborated those conclusions drawn from pedigree analysis and calculated increased inbreeding coefficient values for HERDA horses relative to a random sampling of American Quarter Horses [Tryon et al., *Am J Vet Res,* 66(3): p. 437-42 (2005)]. Analysis of sire records of stallions known to produce offspring with HERDA estimated a carrier frequency of 2-6% in the sub-population of mares being bred to those horses.

The HERDA phenotype shares similarities with clinical diagnoses seen in humans and animals, yet specific features of the disease pathology suggest it may have a unique genetic basis. Ehlers-Danlos Syndrome (EDS) is a heterogenic disorder that can take a variety of forms in humans, but a universal characteristic of the condition is fragile hyperextensible skin that can be more easily subject to bruising and tearing [Mao, J. R. and J. Bristow, *J Clin Invest,* 107(9): p. 1063-9 (2001)]. Many forms of EDS affect skin regardless of the location on the body and do not require a trigger event to display the phenotype. The common thread to the variety of genes in which mutations have been associated with EDS is the fibril collagens. The majority of cases displaying the gross EDS phenotype are caused by defects in the collagen genes themselves (COL1A1, COL3A1, COL5A, COL5A2) or in the enzymes which process (ADAMTS2, PLOD) or interact (TNXB) with collagens.

In contrast, HERDA foals rarely show indications of the disease at birth and areas which develop lesions are non-uniformly distributed over the body. Many cases of HERDA are not identified until the horses begin to train with a saddle, and lesions are most commonly found along the dorsal aspect, coincident with where the saddle would rest. Histological examination of HERDA tissue could not definitively diagnose the disease, although subtle signs of thinned and shortened collagen fibers in the deep dermis suggest a general disorganization in affected individuals [White et al., *Vet Dermatol,* 15(4): p. 207-17 (2004)]. Collagen 1 and collagen 3 content were indistinguishable between HERDA samples and unaffected controls [White et al., *Vet Dermatol,* 15(4): p. 207-17 (2004)].

Thus, there is a need in the art for compositions and methods for accurately identifying equines that are HERDA carriers as well as for diagnosing whether an equine is afflicted with HERDA. The present invention meets these and other needs.

BRIEF SUMMARY OF THE INVENTION

The present invention provides compositions and methods for detecting a single nucleotide polymorphism (SNP) associated with hereditary equine regional dermal asthenia (HERDA).

One embodiment of the invention provides methods for detecting a single nucleotide polymorphism (SNP) associated with hereditary equine regional dermal asthenia (HERDA) phenotype in an equine. The methods comprise detecting a nucleic acid sequence comprising position 115 of a nucleic acid encoding cyclophilin B (PPIB) in a biological sample from the equine, wherein the presence of a single copy of a G to A substitution at position 115 of the nucleic acid encoding PPIB indicates that the equine is a carrier for the SNP associated with HERDA and the presence of two copies of a G to A substitution at position 115 of the nucleic acid encoding PPIB indicates that the animal is affected with HERDA. In some embodiments, the equine is a domesticated equine (e.g., of the genus and subgenus *Equus*). In some embodiments, the nucleic acid is detected by (a) specifically amplifying a nucleic acid sequence comprising position 115 of a polynucleotide encoding PPIB, thereby amplifying nucleic acids comprising the SNP associated with HERDA; and (b) detecting the amplified nucleic acids, thereby detecting the SNP associated with HERDA. In some embodiments, the nucleic acid comprises the sequence set forth in SEQ ID NO:2. In some embodiments, the nucleic acid sequence is specifically amplified using primers comprising the sequences set forth in SEQ ID NOS: 4 and 5. In some embodiments, the SNP is detected by sequencing the amplified nucleic acids. In some embodiments, the SNP is detected by contacting the amplified nucleic acids with EarI.

Another embodiment of the invention provides a kit for detecting a SNP associated with HERDA comprising: (a) an isolated polynucleotide comprising position 115 of a polynucleotide encoding PPIB; and (b) primers that specifically amplify the nucleic acid. In some embodiments, the nucleic acid sequence comprises SEQ ID NOS:1, 2, 3 or a complement or subsequence thereof. In some embodiments, the primers comprise the sequences set forth in SEQ ID NOS:4 and 5. In some embodiments, the kit further comprises the restriction enzyme EarI.

Yet another embodiment of the invention comprises an isolated polynucleotide comprising the sequence set forth in SEQ ID NO:2 or a complement or a subsequence thereof. The invention also provides polypeptide encoded by the isolated polynucleotide, expression vectors comprising the polynucleotide operably linked to an expression control sequence, and host cells comprising the expression vectors. The invention further provides an isolated polynucleotide capable of distinguishing between the sequence provided in SEQ ID NO: 2, or a complement thereof and a nucleic acid encoding a wild type PPIB protein.

A further embodiment of the invention provides an isolated nucleic acid sequence comprising a sequence set forth in Tables 1 and 7.

These and other embodiments of the invention are further described by the detailed description that follows.

BRIEF DESCRIPTION OF THE DRAWINGS AND TABLES

FIG. 3 illustrates the establishment of a minimum critical interval (i.e., fine structure mapping) used to identify PPIB*HRD.

FIG. 6 illustrates a protein sequence alignment of the first 100 residues of PPIB from a HERDA-affected horse (SEQ ID NO:6), a normal horse (SEQ ID NO:7), five mammals (SEQ ID NOS:8-12) and three non-mammalian vertebrates (SEQ ID NO:13-15). The two mutations detected in HERDA-affected horses are indicated with an asterisk.

Figure 1:
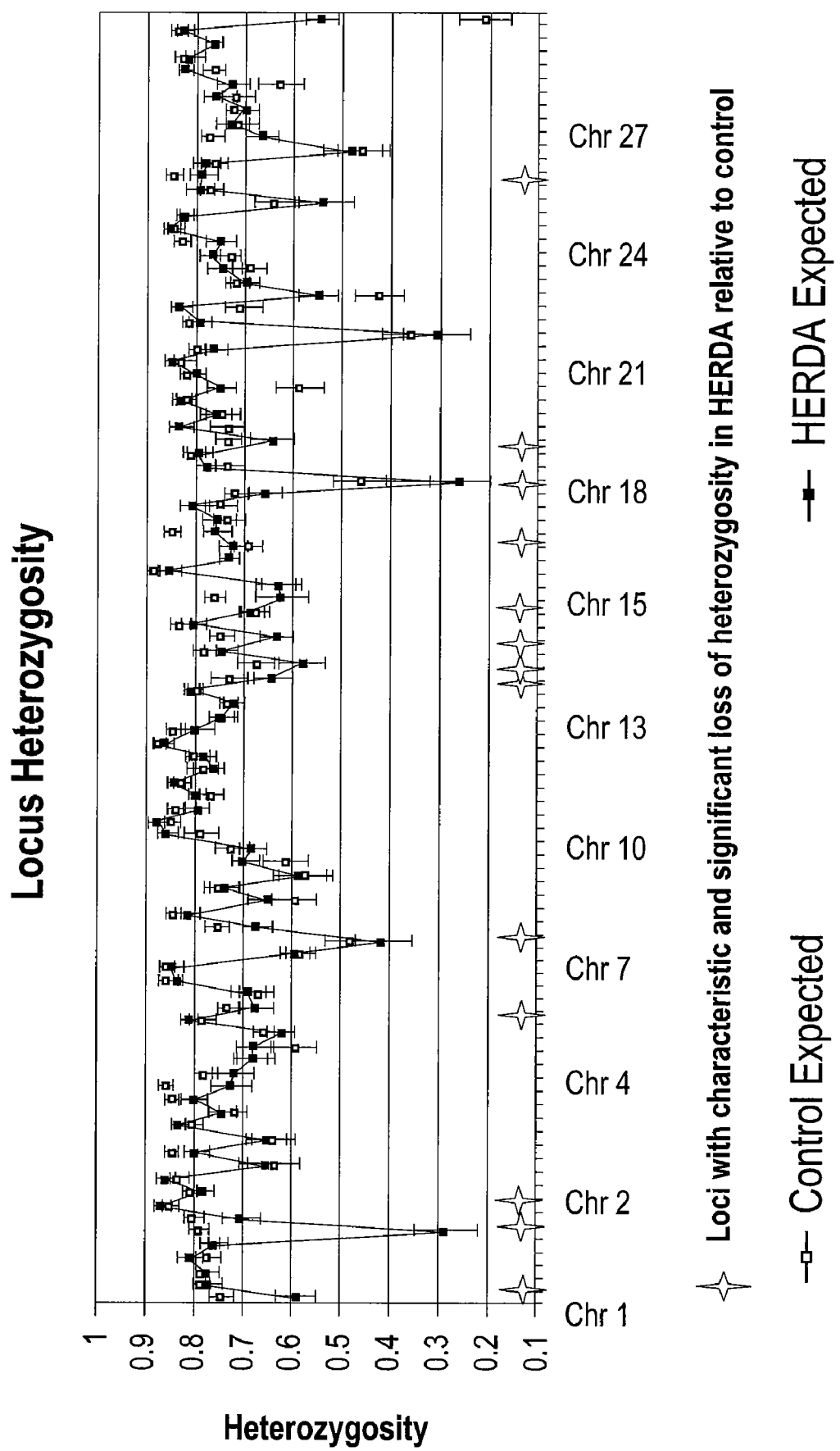
FIG. 1 illustrates a comparison of expected heterozygosity values between populations.

Table 1 sets forth informative SNPs for reducing the critical interval surrounding the HERDA locus. Primers=SEQ ID NOS:16, 17, 20, 21, 24, 25, 26, 27, 30 and 31, respectively; SNP w/Flanking Sequence=SEQ ID NOS:18, 19, 22, 23, 28, 29, 32, 33, respectively.

Table 2 summarizes results from a $\chi^2$ test of differences in allele frequencies between a sample of HERDA-affected horses and age-matched unaffected Quarter Horses Table 3 summarizes results from the PPIB SNP2 genotypes in tested animals.

Table 4 sets forth the primer concentrations and annealing temperatures for the genome scan multiplex reactions described in Example 1 below.

Table 5 primer concentrations and annealing temperatures for the fine structure mapping reactions described in Examples 1 and 3 below.

Table 6 sets forth the top BLAST results for equine microsatellites to human genomic DNA.

Table 7 sets forth sequences for equine PPIB primers (SEQ ID NOS:34-46).

BRIEF DESCRIPTION OF SEQUENCES

SEQ ID NO: 1 is the wild type genomic sequence containing the equine PPIB locus. Introns are presented in lower case and exons are presented in upper case. Positions +1, +2, and +3 (i.e., encoding the Met start codon) are indicated in bold and underlined, position +17 is indicated in bold, position +115 is indicated in bold; primer sequences that can be used to amplify a subsequence of SEQ ID NO: 1 comprising position +115 are underlined.

SEQ ID NO: 2 is the HERDA PPIB cDNA coding sequence. Positions 17 and 115 are indicated in bold.

SEQ ID NO: 3 is the wild type PPIB cDNA coding sequence. Positions 17 and 115 are indicated in bold.

SEQ ID NO: 4 is the sequence of a PCR forward primer used to amplify a region of DNA containing SNP2 (i.e., PPIB*HRD).

SEQ ID NO: 5 is the sequence of a PCR reverse primer used to amplify a region of DNA containing SNP2 (i.e., PPIB*HRD).

DETAILED DESCRIPTION OF THE INVENTION

I. Introduction

The present invention provides compositions and methods for the detection of Hereditary Equine Regional Dermal Asthenia (HERDA) in equine species based on the detection of a single nucleotide polymorphism (SNP) in the cyclophilin B (PPIB) gene that can be used as a marker to identify HERDA carriers and HERDA-affected individuals. The invention is based on identification of a SNP causatively associated with HERDA, i.e., a G→A substitution at position 115 of the cDNA encoding cyclophilin B (i.e., PPIB) gene.

A unique strategy was used to map the HERDA locus which exploited the dataset available, one which consisted of many HERDA-affected horses but few relatives and only a single complete full-sib family which segregated for the trait. A genome scan to identify areas of homozygosity common to HERDA-affected HERDA horses was carried out with the goal of roughly mapping the disease locus. Microsatellites were used to verify that the HERDA locus could be found on the q arm of ECA1, in close proximity to the marker AHT58. Single nucleotide polymorphisms (SNPs) were discovered in genes predicted to lie within a ~20 MB interval surrounding AHT58 and allowed the further reduction of the critical interval to ~2.3 MB, which is predicted to contain 20 known genes based on the comparative genomics of sequenced mammals to date (human, mouse, dog, and cow). These analyses identified, inter alia, a PPIB allele (i.e., PPIB*HRD) comprising a single nucleotide polymorphism (SNP) that is found in perfect association with the HERDA phenotype (i.e., is the causative SNP). The PPIB*HRD SNP is located at position +115 of SEQ ID NO:1 (i.e., a genomic sequence encoding PPIB) and position 115 of SEQ ID NO:2 (i.e., a cDNA sequence encoding PPIB) and is predicted to cause a glycine to arginine missense mutation at position 39 of the encoded polypeptide.

The PPIB*HRD allele can conveniently be used to determine whether a horse exhibiting skin irregularities is HERDA-affected or is a HERDA carrier. For example, when a young horse begins to show skin irregularities, the methods described herein can be used to determine whether or not the horse is HERDA-affected and prevent a potentially unnecessary euthanasia. The methods of the invention can also be used to identify HERDA carriers within the breeding population and minimize the production of HERDA-affected horses.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Equine" as used herein refers to domesticated and wild horses, ponies, burros, and donkeys (e.g., of the Genus *Equus*, including, for example, *Equus Equus caballus, Equus Equus przewalskii, Equus Asinus africanus, Equus Asinus hemionus, Equus Hippotigris burchelli, Equus Hippotigris zebra,* and *Equus Dolichohippus grevyi.*). Horses include any known breed of horse, including, for example, American Quarter Horses, Arabians, Palominos, American Paint Horses, American Wild Horses, Appaloosas, Morgans, Mustangs, Australian Stock Horses, Barbs, Miniature Horses, Thoroughbreds, ponies such as Quarter Ponies, Shetland Ponies, Chincoteague Ponies, and Connemara Ponies, and draft horses such as Clydesdales, American Creams, Belgians, Percherons, Shires, and Suffolks.

"PPIB," "peptidylprolyl isomerase B" and "cyclophilin B" as used herein refers to a member of the peptidyl-prolyl isomerase (PPI) gene family. This family of genes is implicated in protein folding, immune response via its binding of cyclosporine A, and T cell activation. PPIs have been implicated in protein folding of collagens via their cis-trans peptidyl-prolyl isomerase function (see, e.g, Bachinger, *J Biol Chem* 262: 17144-8 (1987); Smith et al., *J. Biol. Chem.* 270: 18323-8 (1995); and Steinmann et al., *J. Biol. Chem.* 266: 1299-303 (1991)). PPIB refers to nucleic acids and polypeptide polymorphic variants (including single nucleotide polymorphisms involving displacement, insertion, or deletion of a single nucleotide that may or may not lead to a change in an encoded polypeptide sequence), alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a PPIB nucleic acid (for an equine PPIB nucleic acid sequence, see, e.g., SEQ ID NOS: 1, 2, and 3 and Genbank Accession No. EF397503); (2) bind to antibodies, e.g., polyclonal antibodies, raised against an immunogen comprising an amino acid sequence of a PPIB polypeptide (e.g., encoded by SEQ ID NOS: 1, 2, or 3), and conservatively modified variants thereof; (3) specifically hybridize under stringent hybridization conditions to an anti-sense strand corresponding to a nucleic acid sequence encoding a PPIB protein, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a PPIB nucleic acid. PPIB nucleic acids include polynucleotides comprising the PPIB SNP causatively associated with HERDA (i.e., PPIB*HRD) as well as polynucleotides comprising PPIB SNPs not causatively associated with HERDA (e.g., PPIB*1). Positions within the PPIB nucleic acids are counted from the adenosine nucleotide of the ATG start codon. A polynucleotide or polypeptide sequence is typically from a mammal including, but not limited to, domesticated equines and wild equines. The nucleic acids and proteins of the invention include both naturally occurring or recombinant molecules.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A nucleic acid "capable of distinguishing" as used herein refers to a polynucleotide(s) that (1) specifically hybridizes under stringent hybridization conditions to an anti-sense strand corresponding to a nucleic acid sequence encoding a PPIB protein, and conservatively modified variants thereof; or (2) has a nucleic acid sequence that has greater than about 80%, 85%, 90%, 95%, preferably greater than about 96%, 97%, 98%, 99%, or higher nucleotide sequence identity, preferably over a region of at least about 25, 50, 100, 200, 500, 1000, or more nucleotides, to a PPIB nucleic acid (e.g., a sequence as set forth in SEQ ID NOS: 1, 2, 3 or complement or a subsequence thereof, including, e.g., a subsequence comprising position 115 of SEQ ID NOS 2 or 3 or position +115 of SEQ ID NO: 1).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point I for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated PPIB nucleic acid is separated from open reading frames that flank the PPIB gene and encode proteins other than PPIB. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region a region of SEQ ID NOS: 1, 2, or 3 or a polypeptide encoded by SEQ ID NOS: 1, 2, or 3), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to PPIB nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

By "host cell" is meant a cell that contains an expression vector and supports the replication or expression of the expression vector. Host cells may be, for example, prokaryotic cells such as *E. coli* or eukaryotic cells such as yeast or CHO cells.

III. Nucleic Acids Encoding PPIB

A. General Recombinant DNA Methods

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding PPIB

In general, the nucleic acid sequences encoding PPIB and related nucleic acid sequence homologues are cloned from cDNA and genomic DNA libraries or isolated using amplification techniques with oligonucleotide primers. For example, PPIB sequences are typically isolated from nucleic acid (genomic or cDNA) libraries by hybridizing with a nucleic acid probe, the sequence of which can be derived from SEQ ID NO: 1, 2, 3, or a complement or a subsequence thereof. PPIB RNA and cDNA can be isolated from any equine.

PPIB polymorphic variants, alleles, and interspecies homologues that are substantially identical to PPIB can be isolated using PPIB nucleic acid probes and oligonucleotides under stringent hybridization conditions, by screening libraries. Alternatively, expression libraries can be used to clone PPIB polymorphic variants, alleles, and interspecies homologues, by detecting expressed homologues immunologically with antisera or purified antibodies made against the core domain of PPIB which also recognize and selectively bind to the PPIB homologue.

To make a cDNA library, PPIB mRNA may be purified from any equine. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 1-8 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *PNAS USA.*, 72:3961-3965 (1975).

An alternative method of isolating PPIB nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of PPIB directly from mRNA, from cDNA, from genomic libraries or cDNA libraries. Degenerate oligonucleotides can be designed to amplify PPIB homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of PPIB encoding mRNA in physiological samples, for nucleic acid sequencing, or for other purposes. Genes amplified by the PCR reaction can be purified from agarose gels and cloned into an appropriate vector.

Amplification techniques using primers can also be used to amplify and isolate PPIB DNA or RNA. For example, nucleic acids encoding PPIB or fragments thereof may be obtained by amplification of an equine cDNA library or reverse transcribed from an equine RNA using isolated nucleic acid primer pairs having the sequences set forth in Table 7 or SEQ ID NOS: 4 and 5.

These primers can be used, e.g., to amplify either the full length sequence or a probe of one to several hundred nucleotides, which is then used to screen a cDNA library for full-length PPIB.

Gene expression of PPIB can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant PPIB genes for use as probes or for expression of protein. This method is performed using a series of overlapping oligonucleotides usually 40-120 bp in length, representing both the sense and non-sense strands of the gene. These DNA fragments are then annealed, ligated and cloned. Alternatively, amplification techniques can be used with precise primers to amplify a specific subsequence of the PPIB gene. The specific subsequence is then ligated into an expression vector. PPIB chimeras can be made, which combine, e.g., a portion of PPIB with a portion of a heterologous PPIB to create a chimeric, functional PPIB.

The gene for PPIB is typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding PPIB proteins comprise a nucleic acid sequence encoding a PPIB protein and subsequences, interspecies homologues, alleles and polymorphic variants thereof. In preferred embodiments, the isolated nucleic acid encoding a PPIB protein is SEQ ID NO: 1, 2, 3 or a complement thereof.

C. Expression of PPIB

To obtain high level expression of a cloned gene, such as those cDNAs encoding PPIB, one typically subclones PPIB into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the PPIB protein are available in, e.g., *E. coli*, *Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the PPIB encoding nucleic acid in host cells. A typical expression cassette thus contains a promoter operably linked to the nucleic acid sequence encoding PPIB and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of PPIB protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing PPIB.

After the expression vector is introduced into the cells, the transfected cells are cultured under conditions favoring expression of PPIB, which is recovered from the culture using standard techniques identified below.

D. Purification of PPIB Protein

Either naturally occurring or recombinant PPIB can be purified for use in functional assays. Naturally occurring PPIB are purified, e.g., from equines and any other source of a PPIB homologue. Recombinant PPIB is purified from any suitable expression system.

PPIB may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant PPIB is being purified. For example, proteins having established molecular adhesion properties can be reversible fused to PPIB. With the appropriate ligand, PPIB can be selectively adsorbed to a purification column and then freed from the column in a relatively pure form. The fused protein is then removed by enzymatic activity. Finally PPIB could be purified using immunoaffinity columns.

IV. Determining Whether an Equine is a HERDA Carrier by Detecting PPIB Nucleic Acid Sequences In one embodiment of the invention, methods of determining whether a particular equine is normal, a HERDA carrier, or HERDA-affected are provided. According to the methods of the invention, the PPIB allele of the equine is analyzed and compared to the PPIB alleles disclosed herein to determine whether the equine is a HERDA carrier. Determination of the presence of absence of a particular PPIB allele is generally performed by analyzing a nucleic acid sample that is obtained from the equine. Often, the nucleic acid sample comprises genomic DNA. It is also possible to analyze RNA samples for the presence of PPIB alleles.

In some embodiments, the PPIB*HRD allele is detected using direct sequencing of an amplified nucleic acid comprising a subsequence of a nucleic acid encoding PPIB (e.g., a nucleic acid comprising position +115 of SEQ ID NO:1 or position 115 of SEQ ID NO:2). Primers can be designed which amplify a nucleic acid comprising position 115 of a PPIB nucleic acid. For example, sequences comprising the PPIB SNP described herein can be amplified using primers comprising the sequences set forth in SEQ ID NOS: 4 and 5. The primers amplify a 250 bp PPIB fragment comprising the PPIB SNP associated with HERDA (i.e., by amplifying a PPIB fragment comprising position +115 of SEQ ID NO:1 or position 115 of SEQ ID NO:2). Once amplified, the sequences can be detected using any method known in the art.

In some embodiments, the PPIB*HRD allele is detected using restriction fragment length polymorphism (RFLP) analysis. For example, sequences comprising the PPIB SNP described herein can be amplified using primers comprising the sequences set forth in SEQ ID NOS: 4 and 5. The primers amplify a 250 bp PPIB fragment comprising the PPIB SNP associated with HERDA (i.e., by amplifying a PPIB fragment comprising position +115 of SEQ ID NO:1 or position 115 of SEQ ID NO:2). Equines carrying wild-type PPIB have an EarI site +34-39 of a genomic PPIB sequence. Equines carrying the PPIB SNP associated with HERDA have an additional EarI site 67 bp from the first EarI site, i.e., at position +111-116 of a genomic PPIB sequence. A PPIB sequence or subsequence comprising is amplified from a biological sample from an equine and the amplification products are digested with a restriction enzyme (i.e., EarI). If the second EarI recognition site is present in the PPIB, the amplification product will be digested in two places. Conversely, if the second EarI recognition site is not present in the PPIB, the amplification products will only be digested in one place. Following digestion, the restriction fragments are then analyzed using any methods known in the art including, for example, gel electrophoresis.

In some embodiments, the PPIB allele is detected using oligonucleotide primers and/or probes (i.e., primers and probes that amplify and detect position 115 of SEQ ID NOS 2 or 3 or position +115 of SEQ ID NO:1). For example, nucleic acids encoding PPIB alleles or fragments thereof may be amplified using isolated nucleic acid primer pairs comprising the sequences set forth in SEQ ID NOS: 4 and 5. Oligonucleotides can be prepared by any suitable method, including chemical synthesis. Oligonucleotides can be synthesized using commercially available reagents and instruments. Alternatively, they can be purchased through commercial sources. Methods of synthesizing oligonucleotides are well known in the art (see, e.g, Narang et al., *Meth. Enzymol.* 68:90-99, 1979; Brown et al., *Meth. Enzymol.* 68:109-151, 1979; Beaucage et al., *Tetrahedron Lett.* 22:1859-1862, 1981; and the solid support method of U.S. Pat. No. 4,458,066).

A. PCR Identification of PPIB Alleles

In some embodiments, PCR is used to amplify nucleic acids encoding PPIB alleles (i.e., wild type PPIB or PPIB alleles comprising PPIB*HRD or PPIB*1). A general overview of the applicable technology can be found in PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683, 195 and 4,683,202.

PCR permits the copying, and resultant amplification of a target nucleic acid, e.g., a nucleic acid encoding PPIB. Briefly, a target nucleic acid, e.g. DNA from a sample from an equine, is combined with a sense and antisense primers, dNTPs, DNA polymerase and other reaction components. (See, Innis et al., supra) The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

B. Detection of Amplified Products

Amplified products can be detected using any means known in the art, including, e.g., restriction fragment length polymorphism (RFLP) analysis; denaturing gel electrophoresis (see, e.g., Erlich, ed., PCR TECHNOLOGY, PRINCIPLES AND APPLICATIONS FOR DNA AMPLIFICATION, W. H. Freeman and Co, New York, 1992, Chapter 7), direct sequencing, and HPLC-based analysis. Suitable sequence methods include e.g., dideoxy sequencing-based methods and Maxam and Gilbert sequence (see, e.g., Sambrook and Russell, supra). Suitable HPLC-based analyses include, e.g., denaturing HPLC (dH-PLC) as described in e.g., Premstaller and Oefner, *LC-GC Europe* 1-9 (July 2002); Bennet et al., *BMC Genetics* 2:17 (2001); Schrimi et al., *Biotechniques* 28(4):740 (2000); and Nairz et al., *PNAS USA* 99(16):10575-10580 (2002); and ion-pair reversed phase HPLC-electrospray ionization mass spectrometry (ICEMS) as described in e.g., Oberacher et al.; *Hum. Mutat.* 21(1):86 (2003). Other methods for characterizing single base changes in PPIB alleles include, e.g., single base extensions (see, e.g., Kobayashi et al, *Mol. Cell. Probes,* 9:175-182, 1995); single-strand conformation polymorphism analysis, as described, e.g, in Orita et al., *Proc. Nat. Acad. Sci.* 86, 2766-2770 (1989), allele specific oligonucleotide hybridization (ASO) (e.g., Stoneking et al., *Am. J. Hum. Genet.* 48:70-382, 1991; Saiki et al., *Nature* 324, 163-166, 1986; EP 235,726; and WO 89/11548); and sequence-specific amplification or primer extension methods as described in, for example, WO 93/22456; U.S. Pat. Nos. 5,137,806; 5,595, 890; 5,639,611; and U.S. Pat. No. 4,851,331; 5'-nuclease assays, as described in U.S. Pat. Nos. 5,210,015; 5,487,972; and 5,804,375; and Holland et al., 1988, *Proc. Natl. Acad. Sci. USA* 88:7276-7280.

Detection techniques for evaluating nucleic acids for the presence of a single base change involve procedures well known in the field of molecular genetics. Further, many of the methods involve amplification of nucleic acids. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1994-1999, including supplemental updates through April 2004; Sambrook & Russell, *Molecular Cloning, A Laboratory Manual* (3rd Ed, 2001).

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the PPIB mutations described herein.

Although the methods typically employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

V. Kits

PPIB and its homologues are useful tools for more specific and sensitive identification of equines that are normal, HERDA carriers, or HERDA-affected. For example, nucleic acids that specifically hybridize to PPIB nucleic acids, such as PPIB probes and primers (e.g., SEQ ID NOS: 4 and 5), PPIB nucleic acids (e.g. nucleic acids comprising a sequence set forth in SEQ ID NOS: 1, 2, 3 or a complement or subsequence thereof) can be used to identify equines that are HERDA carriers.

The invention also provides kits and solutions for detecting the PPIB SNPs described herein. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of PPIB nucleic acid.

Kits can include, for instance, amplification reagents comprising primers sufficient to amplify at least one PPIB PPIB SNP (e.g., SEQ ID NOS: 4 and 5) and at least one probe for amplifying and detecting the polynucleotide sequence. In some embodiments, the kits further comprise a restriction enzyme (e.g., Ear I). In addition, the kit can include nucleotides (e.g., A, C, G and T), a DNA polymerase and appropriate buffers, salts and other reagents to facilitate amplification reactions.

EXAMPLES

The following examples are offered to illustrate, but not to limit the claimed invention.

Example 1

Materials and Methods

Samples: Diagnosed cases of HERDA were referred to us at the UC-Davis Veterinary Medical Teaching Hospital (VMTH) beginning in 1998, and case history, pedigrees, and blood samples were collected. Occasionally owners of affected horses would also include blood samples from parents, siblings, or other first degree relatives. American Quarter Horses are regularly seen at the UC-Davis VMTH and blood samples were collected between 2002-2004. Medical records of these control samples were screened to insure no history of a HERDA phenotype and to verify age. With the permission of the American Quarter Horse Association (AQHA), backlogged hair root samples of specific relatives of affected horses were made available from the UC-Davis Veterinary Genetics Laboratory (VGL), which conducts parentage testing for all registered American Quarter Horses. Genomic DNA was isolated from blood samples using the Qiagen Blood Mini-Kit (Qiagen: Valencia, Calif.). Genomic DNA was isolated from the hair root samples by the VGL using published protocols (Locke et al., *Anim Genet*, 33(5): p. 329-37 (2002)). In total, the dataset consisted of 68 horses diagnosed with HERDA, 76 relatives of affected horses, 1,079 control Quarter Horses, and 55 horses of diverse heritage (e.g., Arabians, Paint Horses, and draft horses).

Microsatellite Genotyping: Fluorescently labeled primers sets for the majority of the microsatellite markers used in the initial scan for homozygosity were obtained with the help of the Dorothy Havermeyer Foundation. Primers for additional published microsatellite markers were obtained from Applied Biosytems (Foster City, Calif.). All microsatellite data was analyzed using an ABI 3100 Genetic Analyzer and STRAND software.

Multiplex reactions for the initial genome scan were based on previous reports (Locke et al., *Anim Genet*, 33(5): p. 329-37 (2002)]. Data for 27 of the 100 loci screened in the genome scan were generated by the VGL as part of their standard parentage panel and genotyped in three multiplex reactions. Sixty-six additional markers were combined into fourteen multiplex reactions. Amplification of genome scan multiplex reactions were performed in 25 μL total volume containing 1 μL genomic DNA, 1×PCR buffer, 2.5 mM $MgCl_2$, 250 μM dNTPs, 1 unit AmpliTaq Gold (Applied Biosystems) with primer concentrations and annealing temperatures specified in Table 4. The other seven microsatellites were individually amplified and genotyped under the same conditions except for a reduced total volume of 15 μL and 0.5 units AmpliTaq Gold. For fine structure mapping around the HERDA locus, informative markers spanning ECA1 were combined into small multiplex reactions to minimize sample use. Amplification conditions were in 20 μL total volume, 1 μL genomic DNA, 1× PCR Buffer, 1.5 mM $MgCl_2$, 125 μM dNTPs, 0.5 units AmpliTaq Gold with primer concentrations and annealing temperatures specified in Table 5.

Statistics: Allele and genotype frequencies were counted within the control population (n=44) and the affected population (n=38) at 98 autosomal microsatellite loci. For each group, the expected heterozygosity values with standard errors and observed heterozygosity values of each locus were calculated with Arlequin software (Excoffier et al., *Evolutionary Bioinformatics Online*, (1): p. 47-50 (2005)). A chi-square test of a L×2 contingency table with L-1 degrees of freedom, where L=# of alleles present at a given locus, were conducted to calculate P values testing the null hypothesis that the two population samples have the same allele frequencies. LOD scores were generated using the HOMOZ/MAPMAKER software [Kruglyak et al., *Am J Hum Genet*, 56(2): p. 519-27 (1995)].

Establishing a comparative framework: Equine microsatellites were compared with the human genome using BLAST to determine a comparative framework between the two genomes. A minimal standard of homology between the equine and human sequences was set at an alignment score (S)>60 and a sum probablility value (E)<3.0 E-06 consistent with previous reports (Farber, C. R. and J. F. Medrano, *Anim Genet,* 35(1): p. 28-33 (2004)). Subsequently, the region of the human genome identified with BLAST comparisons, plus 5 MB proximal and distal to the region, were compared with other fully and partially mapped mammalian genomes using the UCSC Genome Browser to confirm conservation of synteny across species.

A list of equine candidate genes was generated from the region of synteny from the human genome (Build 35.1). The Horse Genome Project was searched for equine BAC clones which had both ends successfully sequenced and that BLAST within 250 kB of each other on HSA15, surrounding the region of identity by descent (Leeb et al., *Genomics* 87: 772-776 (2006)). These BAC clones provided additional confidence in the physical relationship between ECA1 and HSA15 and helped to verify our candidate gene list. Equine gene specific markers were optimized with the 5000 rad equine panel (Chowdhary et al., *Genome Res,* 13(4): p. 742-51 (2003)). Informative gene specific markers were subsequently RH mapped to verify their locations relative to previously RH mapped microsatellites UM004, AHT58, and UM043.

SNP discovery and genotyping: A list of genes predicted to lie within the region of homozygosity identified in the HERDA population was generated based on comparative homology across fully sequenced mammals (human, mouse, and dog). Genes for SNP discovery were selected based on their spacing across the region as well as the availability of mammalian mRNA sequences from the Genbank database. Sequences from all available mammals (most often human, mouse, dog, and cow) were aligned (Vector NTI) and analyzed for regions of high conservation across species. In addition, human and mouse mRNA sequences were subjected to BLAT analysis against their respective compiled genomic sequences to determine intron/exon boundaries and the size of introns. Introns which had conserved sizes between 700 bp and 3 Kb in both human and mouse were targeted to facilitate cloning and sequencing. These features were used to design primers for amplification of specific homologous sequences from the horse genome.

Genomic DNA from an unaffected Quarter Horse and an affected HERDA horse were used to amplify corresponding genomic fragments for each of the genes in Table 1. The HERDA sample used in this phase of SNP discovery was homozygous for 10 microsatellite markers which span 31.6 cM. Fragments which amplified cleanly and were of the approximate expected size were cloned into the TOPO TA Cloning Kit (Invitrogen: Carlsbad, Calif.). Three bacterial clones from both the control and affected horse were sequenced with vector specific primers. Sequences were subjected to BLAST analysis to verify that both ends of cloned exonic sequence were homologous to the genes targeted. All clones were aligned to identify gene-specific intronic SNPs or microsatellites which may segregate within the Quarter Horse population. To genotype SNPs from additional affected horses and unaffected controls, genomic fragments were amplified, purified with the Qiaquik Purification Kit (Qiagen: Valencia, Calif.) and sequenced on an ABI 3100 Genetic Analyzer with one of the gene specific primers used in the original amplification. The polymorphic microsatellite within the intron of SPG21 was genotyped using a fluorescently labeled primer as previously described.

Sequencing of candidate genes: Skin fibroblasts derived from dermal punch biopsies (Animal care protocol #10714) taken from an affected HERDA horse and an age-matched unaffected Quarter Horse were used to generate cDNA libraries (Fast Track 2.0 mRNA Isolation Kit, Invitrogen; Marathon cDNA Amplification Kit, BD Biosciences). 5' and 3' RACE reactions were carried out with appropriate reverse and forward primers (Table 7), separated by gel electrophoresis, extracted, and sequenced directly to obtain coding sequence as well as partial 5'UTR and 3'UTR. For PPIB, additional primers were designed to generate sequence of the four predicted introns (Table 7). Equine homologues of human genes from the syntenic region were computationally mined from the equine whole genome sequence trace archives. Discontinuous MegaBLAST was used to design primers that generated maximal equine coding sequence. cDNA products were amplified, cloned, and sequenced to identify additional SNPs between the affected and unaffected cDNA libraries.

Assay for SNP2 (i.e., PPIB*HRD) in PPIB: Primers were designed to amplify a fragment of the cyclophilin B gene which contains an informative SNP from equine gDNA. An unlabeled forward primer (5'CGGTGGATGCTGCGTTTCT; SEQ ID NO:4) and a fluorescently labeled reverse primer (5'6FAM-GCCCAAGCCAGCCTAGGA; SEQ ID NO:5) were used to generate a 250 bp fragment under the following conditions: 1 µL genomic DNA, 1×PCR Buffer (Perkin-Elmer), 1.5 mM $MgCl_2$, 125 µM of each dNTP, primer concentrations of 0.2 µM, and 0.5 units Taq Gold in a 20 µL reaction. Samples were denatured for 10 minutes at 94° C., followed by 32 cycles of 20 sec at 94° C., 30 sec at 58° C., and 1 min at 72° C.; followed by 10 min at 72° C. 10 µL of the PCR reaction was subsequently digested in a total volume of 20 µL containing 1×NEB Buffer 1 and 4 units Ear I restriction endonuclease (NEB) for 2.5 hours at 37° C. 1 µL of digested product was combined with 10 µL of a 5% dilution of Gene Scan 400HD[ROX] in Hi-Di Formamide (Applied Biosystems), denatured for 5 minutes at 94° C., cooled for 5 minutes at 4° C., and analyzed on a 3100ABI Genetic Analyzer. A conserved Earl site which cuts 46 bp from the end of the forward primer serves as an internal control to verify that the enzyme is working properly. The SNP detected in the HERDA population introduces a second Ear I site which cuts an additional 67 bp from the conserved Ear I site. All samples tested are run with a water negative control and three positive controls: (1) an affected HERDA sample; (2) the heterozygous sire of (1); and (3) an unaffected homozygous 'wild-type' full sibling of(1).

Example 2

Mapping HERDA

The initial populations studied consisted of 38 affected HERDA horses, 44 age-matched unaffected Quarter Horses, and 13 first-degree relatives of affected horses. Of 98 loci evaluated, only 13 had distinguishable expected heterozygosity values, based on the overlapping of their standard error, and an unambiguous decrease of observed heterozygosity in the HERDA population relative to the control population (FIG. 1). The remaining 13 loci were further evaluated for significant differences in allele frequencies using a chi-square test of a contingency table comparing the two populations. Only HMS15 and HMS7, two markers which map ~18 cM apart on ECA 1, gave significant P values <0.05 (Table 2).

Figure 2A:
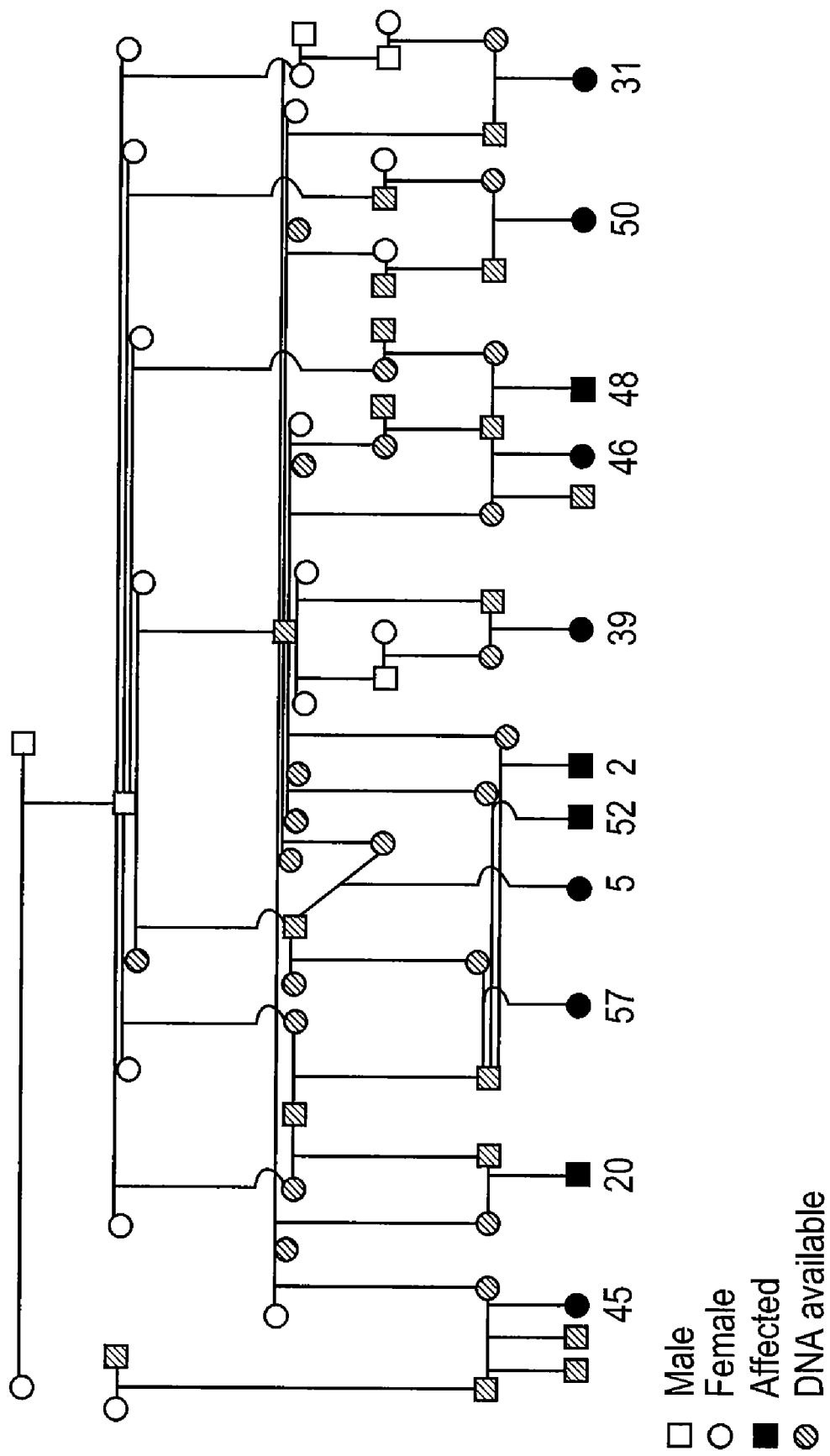
FIG. 2 illustrates (A) the pedigree of families used to confirm the location of the HERDA locus; (B) ECA1 analysis confirming the location of the HERDA locus.
Figure 2B:
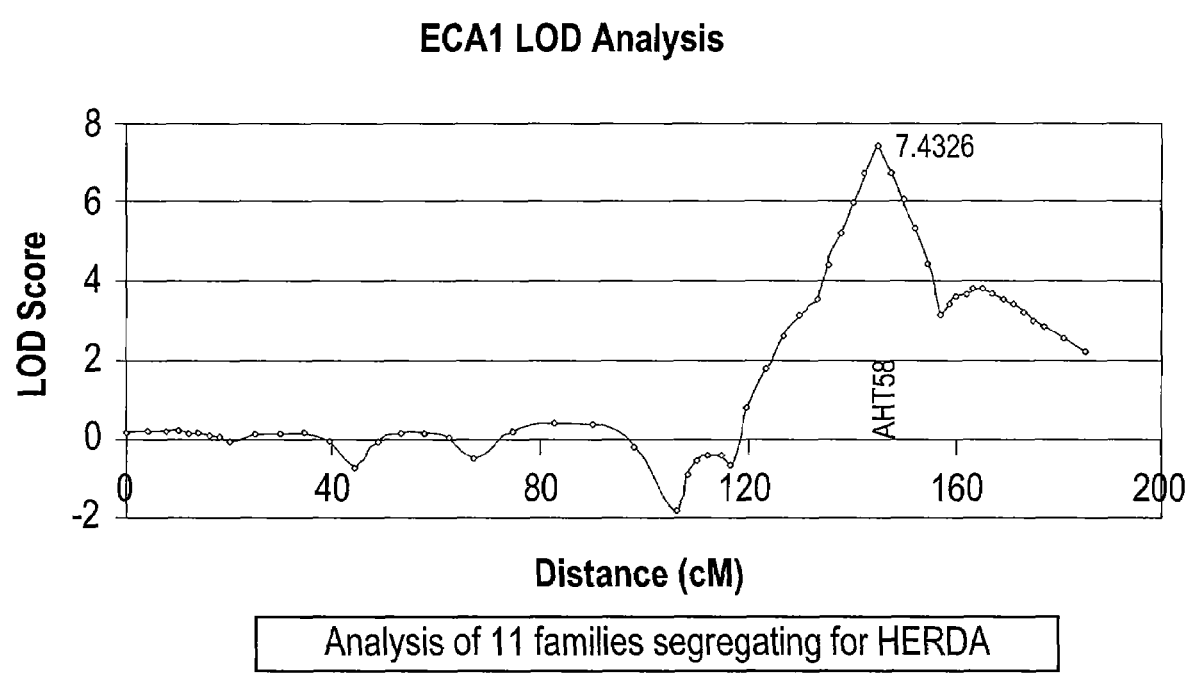

To confirm the location of the HERDA locus, 52 samples consisting of 11 affected and 41 relatives were genotyped at 9 loci on ECA1 (FIG. 2A). The average distance between markers is 16.8 cM and the two markers (HMS15 and HMS7) which were used to initially detect the reduction in heterozygosity within the affected population were replaced by alternative nearby markers for this stage of analysis. A maximum LOD score of 7.4 was generated at marker AHT58 (FIG. 2B). Similar analyses were performed with these samples for a subset of chromosomes which had been analyzed in Table 1 based on early indications of a reduction in heterozygosity. Maximum LOD scores for all loci tested, except those on the distal arm of ECA1, did not approach the minimally significant LOD score of 3.0 typically used in linkage studies.

Example 3

Reduction of the Critical Interval/Fine Structure Mapping

The large number of HERDA samples collected to date (61+7) provides the opportunity to use recombination events which have occurred as the mutant allele has been passed down through the generations to minimize the critical interval that contains the HERDA locus. Initially, 12 microsatellites that have been linkage mapped or RH mapped near the AHT58 marker were used to genotype all HERDA samples. Sixty four (57+7) samples contained a region of homozygosity centered around the AHT58 marker and carry two copies of the 185 allele. Eight (6+2) of these samples were homozygous at all 12 microsatellite markers, a region which spans 31.6 cM, and most likely represent the alleles that were in linkage disequilibrium with the mutation when it arose. The majority of samples contained a large block of homozygosity either proximal or distal to, but always containing the AHT58 microsatellite.

BLAST results of seven of the twelve microsatellites used to refine the area of homozygosity within affected samples established a framework to compare the equine and human genomes (Table 6). UCD440, AHT58, and UM043 showed significant homology to regions of HSA15q22-15q24 (located at approximately 59.9 MB, 62.6 MB, and 71.1 MB respectively), which is consistent with the most recent comparative maps reported (Perrocheau et al., *Anim Genet*, 37(2): p. 145-55 (2006); Swinburne et al., *Genomics*, 87(1): p. 1-29 (2006)). The region of HSA15 was screened for genes associated with EDS or related genes which would be logical candidates based on the observed phenotype. Although no EDS-like candidate genes were evident, cartilage intermediate layer protein (CILP) merited further investigation, despite the appearance of lying outside the critical interval. Additional gene-based markers were discovered within the equine homologues of five human genes (ITGA11, CILP, SPG21, USP3, and TLN2) that map within the region of HSA15. SNPs were found within four of the five gene introns while a polymorphic dinucleotide microsatellite was found within an intron of SPG21 (Table 1).

A subset of 18 affected samples which were informative for defining the critical interval with microsatellites and 5 unaffected, unrelated samples were used for evaluating gene-specific markers. Three affected samples heterozygous for the intronic SNP in TLN2, proximal to the HERDA locus, and six affected samples heterozygous for the intronic dinucleotide repeat in SPG21, distal to the HERDA locus, define the smallest identifiable critical interval to date (FIG. 3).

Example 4

Mutation Screen

Figure 4A:
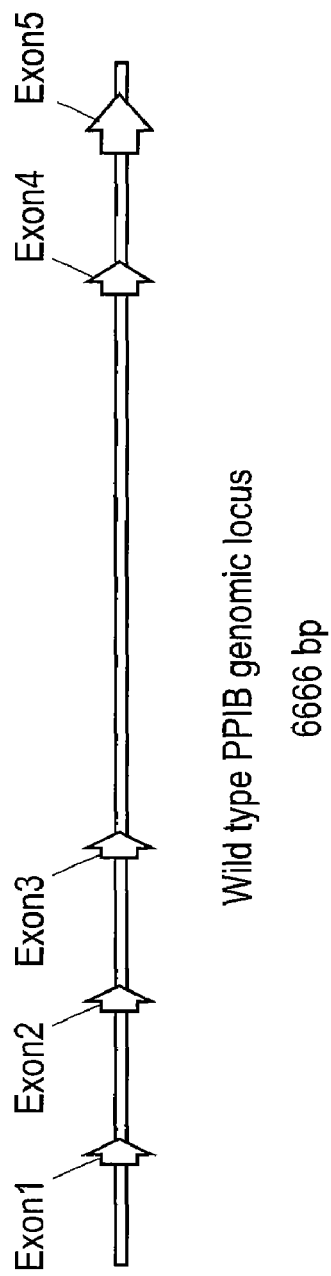
FIG. 4 illustrates (A) the genomic region corresponding to SEQ ID NO: 1; (B) the structure of equine PPIB cDNA.
Figure 4B:
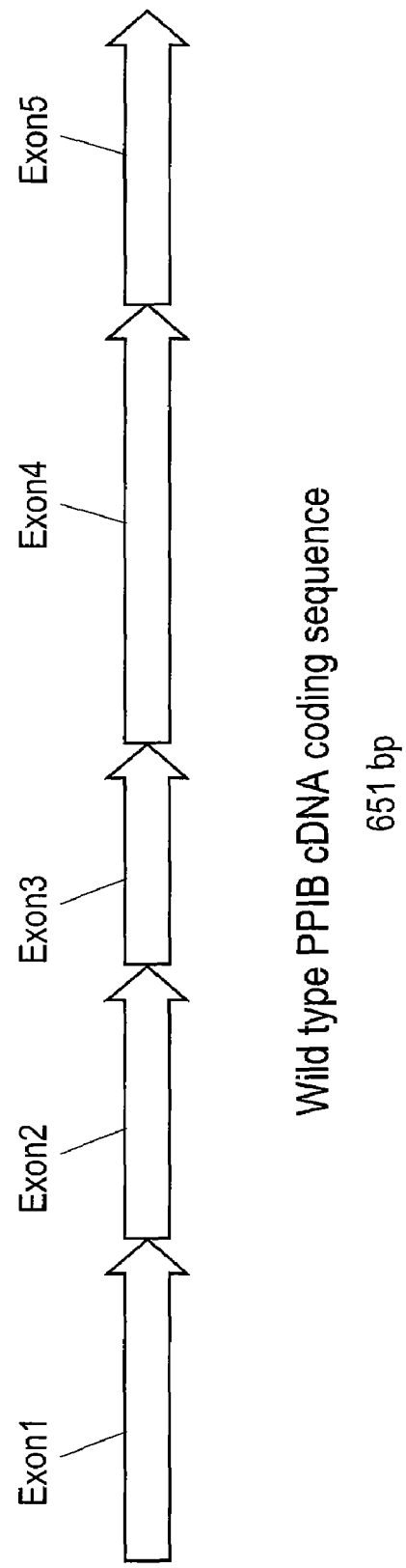

In other species, the minimal critical interval containing the HERDA locus is part of a larger block of synteny which has been conserved throughout evolution based on comparative analysis of human, chimpanzee, rhesus, dog, mouse, and rat genomes. The region, including TLN2 and SPG21, contains 20 known genes and 6 putative loci in humans. Further investigation into the reported functions and protein associations of these genes led to the sequencing of PPIB, or cyclophilin B (FIGS. 4A and 4B).

Figure 5A:
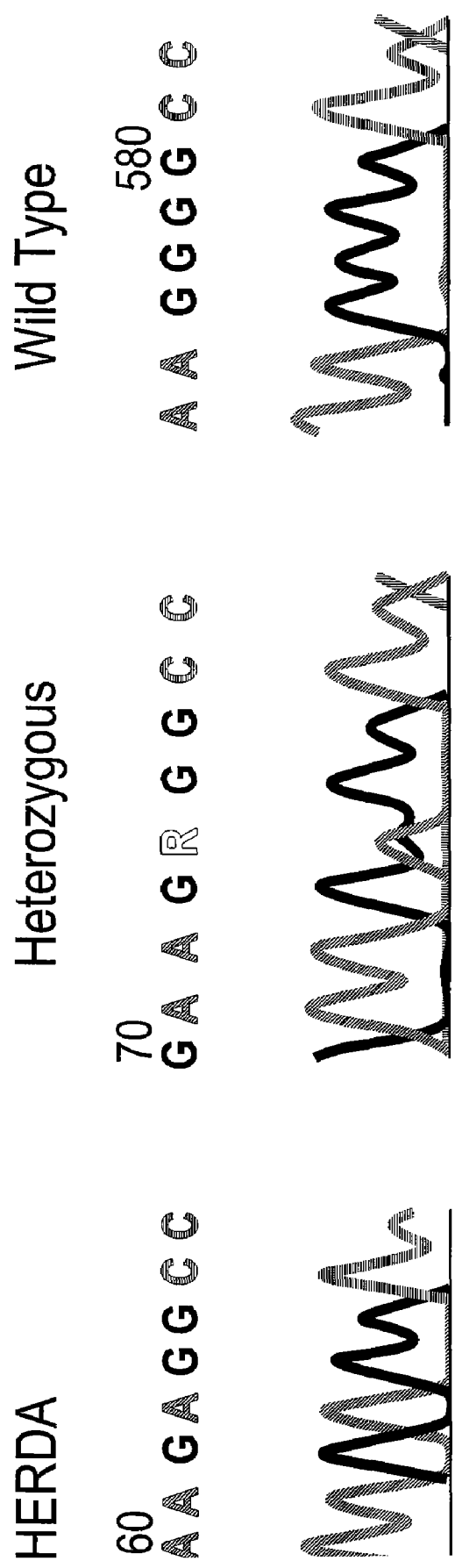
FIG. 5 illustrates (A) the direct sequence of SNP2 in equine cyclophilin B; (B) an assay of SNP2 in equine cyclophilin B.

Two SNPs (i.e., PPIB*1 and PPIB*HRD) which are predicted to cause missense mutations were found by sequencing PPIB cDNA of a HERDA affected horse and comparing it to the PPIB cDNA sequence of an unaffected control horse (Genbank Accession No. EF397503). All four introns of PPIB were also sequenced and no informative SNP's were found. Additional samples were amplified, purified, and sequenced to determine if either of the two SNPs was commonly found in Quarter Horses. SNP1 or PPIB*1 (A17G), predicted to cause a glutamic acid to glycine change in protein sequence (i.e., p. 6E>G) in the putative endoplasmic reticulum (ER) signal sequence, was found in multiple non-affected samples in both the heterozygous and homozygous states, indicating that it is not causative for HERDA. SNP2 or PPIB*HRD (G115A), predicted to cause a glycine to arginine change in protein sequence (i.e., p. 39G>R), was homozygous within affected samples; heterozygous among (14 of 18) non-affected relatives initially screened; and not found among the unaffected, unrelated control samples (FIG. 5A).

Figure 5B:
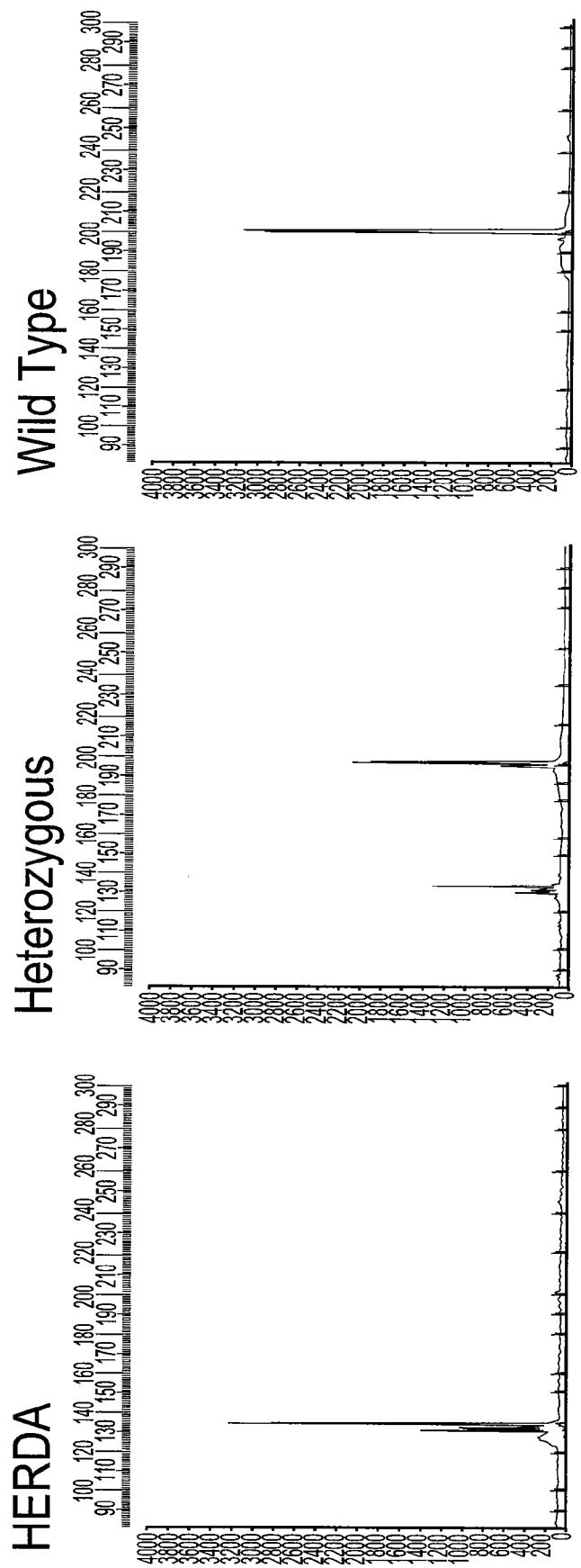

An assay was developed so that large numbers of samples could be screened to determine the frequency of SNP2 (i.e., PPIB*HRD) (FIG. 5B). All HERDA samples, with the exception of the four genotypically distinct samples flagged as potential misdiagnosed cases were homozygous for the mutation (Table 3). All available samples of relatives of affected horses were analyzed and 76% (58 of 76) are heterozygous. All parents of affected horses that are homozygous for the SNP are heterozygous, consistent with the autosomal recessive nature of the disease. Samples which were related (parent or grandparent) to the four genotypically aberrant affected horses were homozygous for the wild type SNP. Previous pedigree analysis of the families used in establishing a LOD score for the HERDA locus typically display an inbreeding loop which represents the most likely path of the transmission of the mutation. In all cases, the SNP segregated in a predictable fashion consistent with the hypothesis that inbreeding is leading to the union of two mutant alleles which are identical by descent.

A set of 182 unaffected Quarter Horses collected at the VMTH were screened for the mutation. Seven samples were heterozygous and 175 were homozygous for the wild type SNP, suggesting a 3.85% carrier frequency. An additional 897 Quarter Horse samples revealed 866 that are homozygous wild type and 31 that are heterozygous, suggesting a 3.46% carrier frequency. A small sampling of Arabians, draft horses, and a set of horses of unknown lineage were tested and only the wild type SNP was detected.

The HERDA predicted PPIB protein and one of the two equine wild type variants were aligned with five mammalian and three non-mammalian vertebrate (*Danio rerio, Xenopus tropicalis*, and *Gallus gallus*) PPIB sequences (FIG. 6). Equine PPIB shared the highest identity (97.7%) with canine PPIB. The six mammalian PPIB sequences were 88% identical. Across sequenced vertebrates, the glycine residue that is mutated in HERDA horses is invariant. The glycine sits in the third position of a completely conserved seven amino acid peptide (37KKGPKVT43; SEQ ID NO:47) structure that has been strictly maintained throughout vertebrate evolution.

It will be recognized by the skilled artisan that a number of methods known in the art may be used to assay for the SNP of the present invention, including, but not limited to, sequencing, pyrosequencing, allele specific PCR, restriction enzyme digestion, and oligonucleotide hybridization, among others.

Example 5

Linked Marker Test

Of the 57 affected samples initially screened and the 7 samples subsequently screened and identified as homozygous for the "HERDA" SNP2 of PPIB (i.e., PPIB*HRD), all samples are homozygous for the 185 allele at marker AHT58. Fifty-three of the initially screened samples and 3 of the subsequently screened samples (93.7% cumulatively) are homozygous for the 115 allele of UM004, suggesting the marker is farther away from the PPIB SNP2 then AHT58.

To investigate the utility of SNP2, the 38 samples from the control Quarter Horse population which were heterozygous for "HERDA" SNP2 were genotyped at the flanking markers AHT58 and UM004. In all cases, the 185 allele of AHT58 and the 115 allele of UM004 were detected. The HERDA haplotype in conjunction with the above data showed that the three markers were tightly associated.

The mapping of disease genes in the horse have benefited greatly from our understanding of human diseases and their previously discovered genetic bases. In the case of HERDA, a number of phenotypic similarities with the heterogenic disorder Ehlers-Danlos Syndrome did not lead us to a short, well-defined list of candidate genes worth pursuing. Instead, unique features of the HERDA pathology which appear to distinguish it from previously reported conditions suggested that a broader approach must be taken to maximize the chance of mapping the locus. In addition, the unusual structure of horse families and populations introduces difficulties in obtaining well-defined, segregating families for a given trait. A combination of approaches, integrating data from the comparative genomics of mammals, allowed the mapping of the HERDA locus to a relatively small, ~2.3 MB region of ECA1.

The detection of homozygous polymorphisms in the HERDA population within the minimum critical interval allowed development of a marker for HERDA. Of the 57+7 affected horses which share the characteristic HERDA haplotype, four DNA markers have been determined to be homozygous in all samples: the G→A intronic SNP of USP3; the A→G exonic SNP (+17) predicted to cause a missense mutation in PPIB(PPIB*1); the G→A exonic SNP (+115) predicted to cause a missense mutation of PPIB(PPIB*HRD); and the 185 allele of the AHT58 microsatellite marker. A C→T intronic SNP in TLN2 and an intronic microsatellite in SPG21 serve as markers for establishing the smallest critical interval surrounding the HERDA locus.

Comparative genomics reveals this region of the mammalian genome to have conserved synteny. The equivalent region of the human genome includes 20 known genes and 6 putative genes, including TLN2 and SPG21. No obvious candidate genes consistent with known EDS genes reside within this region. Additional research into the functions of genes within the region led to the sequencing of PPIB based on its cis-trans peptidyl-prolyl isomerase function and a published association with procollagen [Davis et al., *J Biol Chem*, 264 (15): p. 8956-62 (1989); Smith et al., *J Biol Chem*, 270(31): p. 18323-8 (1995); Steinmann et al., *J Biol Chem*, 266(2): p. 1299-303 (1991)]. A SNP which would change a conserved glycine residue to an arginine in PPIB was found.

The tight association of the G→A exonic SNP (PPIB*HRD) with the HERDA phenotype makes it a highly informative marker for confirming suspected cases of HERDA and screening unaffected horses for carrier status. All parents of HERDA horses that are homozygous for the SNP are heterozygous. Of 1210 unaffected horses screened, none were found to be homozygous for the G→A exonic SNP (PPIB*HRD). In addition, all 38 control horses found to be heterozygous for the SNP carried alleles at the flanking markers consistent with the HERDA haplotype. This observation agrees well with the hypothesis that the SNP developed only once within the American Quarter Horse, presumably in association with the HERDA locus.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for detecting a single nucleotide polymorphism (SNP) associated with hereditary equine regional dermal asthenia (HERDA) phenotype in an equine, the method comprising:
 isolating from the equine a DNA molecule comprising a cyclophilin B (PPIB) sequence at least 95% identical to SEQ ID NO: 1 or an mRNA molecule transcribed from the PPIB sequence; and
 detecting a G to A substitution at position 115 counted from the start codon of the PPIB sequence;
 wherein the presence of a single copy of G to A substitution at position 115 of the PPIB sequence indicates that the equine is carrier for the SNP associated with HERDA and the presence of two copies of a G to A substitution at position 115 indicates that the animal is affected with HERDA.

2. The method of claim 1, wherein said equine is a domesticated equine.

3. The method of claim 1, wherein the G to A substitution is detected by
 a) specifically amplifying a nucleic acid sequence comprising position 115 of the PPIB sequence, thereby amplifying nucleic acids comprising the SNP associated with HERDA; and
 b) detecting the amplified nucleic acids, thereby detecting the SNP associated with HERDA.

4. The method of claim 3, wherein the nucleic acid sequence is specifically amplified using primers comprising the sequences set forth in SEQ ID NOS: 4 and 5.

5. The method of claim 3, wherein the SNP is detected by sequencing the amplified nucleic acids.

6. The method of claim 3, wherein the SNP is detected by contacting the amplified nucleic acids with EarI.

7. The method of claim 3, wherein the step of specifically amplifying the nucleic acid sequence is carried out using reverse transcription and amplification of the mRNA molecule.

* * * * *